United States Patent [19]

Nakada et al.

[11] Patent Number: 5,876,975
[45] Date of Patent: Mar. 2, 1999

[54] TREHALOSE PHOSPHORYLASE ITS PREPARATION AND USES

[75] Inventors: Tetsuya Nakada; Michio Kubota; Hiroto Chaen; Toshio Miyake, all of Okayama, Japan

[73] Assignee: Kabushiki Kaisha Hayashibara Seibutsu Kagaku Kenkyujo, Okayama, Japan

[21] Appl. No.: 103,509

[22] Filed: Jun. 24, 1998

Related U.S. Application Data

[62] Division of Ser. No. 966,389, Nov. 7, 1997.

[30] Foreign Application Priority Data

Nov. 8, 1996 [JP] Japan ................................. 8-311232
Mar. 3, 1997 [JP] Japan ................................. 9-061716

[51] Int. Cl.⁶ ........................... C12P 19/44; C12P 21/06; C12N 9/10; C07K 1/00
[52] U.S. Cl. ................. 435/74; 435/72; 435/95; 435/97; 435/69.1; 435/252.3; 435/320.1; 530/300; 530/350; 536/23.2
[58] Field of Search ................. 435/74, 72, 95, 435/97, 193, 69.1, 252.3, 320.1, 41; 536/23.2; 530/350, 300; 624/679

[56] References Cited

U.S. PATENT DOCUMENTS

4,628,028  12/1986  Katkocin et al. .......................... 435/95
5,643,775   7/1997  Takahashi et al. ...................... 435/193

FOREIGN PATENT DOCUMENTS

7-59584  3/1995  Japan .

OTHER PUBLICATIONS

Gherna et al. (Eds), "Cataloge of Bacteria and Bacteriophages", 18th Ed., American Type Culture Collection (Rockville, MD), pp. v, 366 (1992).

Kizawa et al, "Purification and Characterization of Trehalose Phosphorylase from *Micrococcus varians*", *Biosci. Biotech. Biochem.* 59(10):1908–1912 (1995).

Murao et al, "Enzymatic Synthesis of Trehalose from Maltose", *Agric. Biol. Chem.* 49(7):2113–2118 (1985).

Marechal et al, "Metabolism of Trehalose in *Euglena gracilis*", *J. Biol. Chem.* 247(10):3223–3228 (1972).

Sambrook et al, *Molecular Cloning: A Laboratory Manual*, 2nd. Ed., Cold Spring Harbor Laboratory Press (Cold Spring Harbor, NY, 1989).

Yoshida et al, "Production and Application of Maltose Phosphorylase and Trehalose Phosphorylase by a Strain of *Plesiomonas*", *Oyo Tashitsu Kagaku* 42(1):19–25 (1995).

*Primary Examiner*—Robert A. Wax
*Assistant Examiner*—Tekchand Saidha
*Attorney, Agent, or Firm*—Browdy and Neimark

[57] ABSTRACT

A thermostable trehalose phosphorylase which is obtainable from microorganisms of the genus Thermoanaerobium and which hydrolyzes trehalose in the presence of an inorganic phosphoric acid to form D-glucose and β-D-glucose-1-phosphoric acid. The trehalose phosphorylase can be also prepared by recombinant DNA technology. When the enzyme is allowed to contact with β-D-glucose-1-phosphoric acid as a saccharide donor in the presence of other saccharides, glucosyl-transferred saccharides including glucosyl-D-galactoside, which are conventionally known but scarcely obtainable, can be produced on an industrial-scale and in a relatively-low cost.

5 Claims, 5 Drawing Sheets

TREHALOSE PHOSPHORYLASE ITS PREPARATION AND USES

CROSS-REFERENCE TO RELATED APPLICATION

This is a division of copending patent application Ser. No. 08/966,389, filed Nov. 7, 1997.

BACKGROUND OF THE INVENTION

1. Field of the Invention

The present invention relates to a novel trehalose phosphorylase, its preparation and uses, more particularly, to a novel trehalose phosphorylase which hydrolyzes trehalose in the presence of an inorganic phosphoric acid and/or its salt (hereinafter abbreviated as "inorganic phosphoric acid" throughout the present specification, if not any inconvenience will arise) to form D-glucose and β-D-glucose-1-phosphoric acid and/or its salt (hereinafter abbreviated as "β-D-glucose-1-phosphoric acid" throughout the present specification, if not any inconvenience will arise), and which, in reverse, forms trehalose and inorganic phosphoric acid from β-D-glucose-1-phosphoric acid and D-glucose, and to the processes of the trehalose phosphorylase, saccharide compositions containing glucosyl-transferred saccharides produced by using the trehalose phosphorylase, and compositions containing the saccharide compositions.

2. Description of the Prior Art

Recently, oligosaccharides such as maltose and trehalose and functions thereof have become to be highlighted, and have been studied on their unique and different processes in view of various aspects. It is known that phosphorylases such as maltose, trehalose, sucrose, trehalose, and cellobiose phosphorylases can be used as methods for producing the above oligosaccharides.

L. R. Maréchal et al reported that in "*The Journal of Biological Chemistry*", Vol.247, No.10, pp.3,223–3,228 (1972), *Euglena gracilis* produces trehalose phosphorylase intracellularly; and S. Murao et al reported that in "*Agriculture and Biological Chemistry*", Vol.49, No.7, pp.2,113–2,118 (1985), the properties of the enzyme. K. Aisaka et al disclosed in Japanese Patent Kokai No.59,584/95 a bacterial trehalose phosphorylase which is produced by a microorganism of the species *Catellatospora ferruginea* and one of the species *Kineosporia aurantiaca*. H. Kizawa et al reported that in "*Bioscience, Biotechnology and Biochemistry*", Vol.59, No.10, pp.1,908–1,912 (1995), a microorganism of the species *Micrococcus varians* produces such an enzyme, and M. Yoshida et al reported that in "*Oyo-Toshitsu-Kagaku*", Vol.42, No.1, pp.19–25 (1995), a microorganism of the species *Plesiomonas sp.* SH-35 produces trehalose phosphorylase. Among these trehalose phosphorylases, the enzymes from the microorganisms of the species *Micrococcus varians, Euglena gracilis,* and *Plesiomaonas sp.* have lower thermal stabilities of less than 30°, 40° and 45° C., respectively, resulting both in a relatively-low reaction efficiency on an industrial scale production and in a bacterial contamination during an enzymatic reaction.

SUMMARY OF THE INVENTION

The present invention provides a novel trehalose phosphorylase with an industrially-advantageous thermostability, process thereof, saccharide compositions containing the glucosyl-transferred saccharides prepared by using the enzyme, and uses thereof.

To solve the above object and to obtain an unknown trehalose phosphorylase with a satisfactory thermostability, the present inventors widely screened microorganisms which produce such an enzyme. As a result, they found that *Thermoanaerobium brockii*, ATCC 35047, belonging to the genus Thermoanaerobium, produces a novel trehalose phosphorylase and established the preparation. They also established a saccharide composition containing glucosyl-transferred saccharides produced by contacting the enzyme with β-D-glucose-1-phosphoric acid as a saccharide donor in the presence of saccharides, and compositions containing the saccharide composition. Thus, they accomplished this invention.

BRIEF DESCRIPTION OF THE ACCOMPANYING DRAWINGS

DETAILED DESCRIPTION OF THE INVENTION

Figure 1:
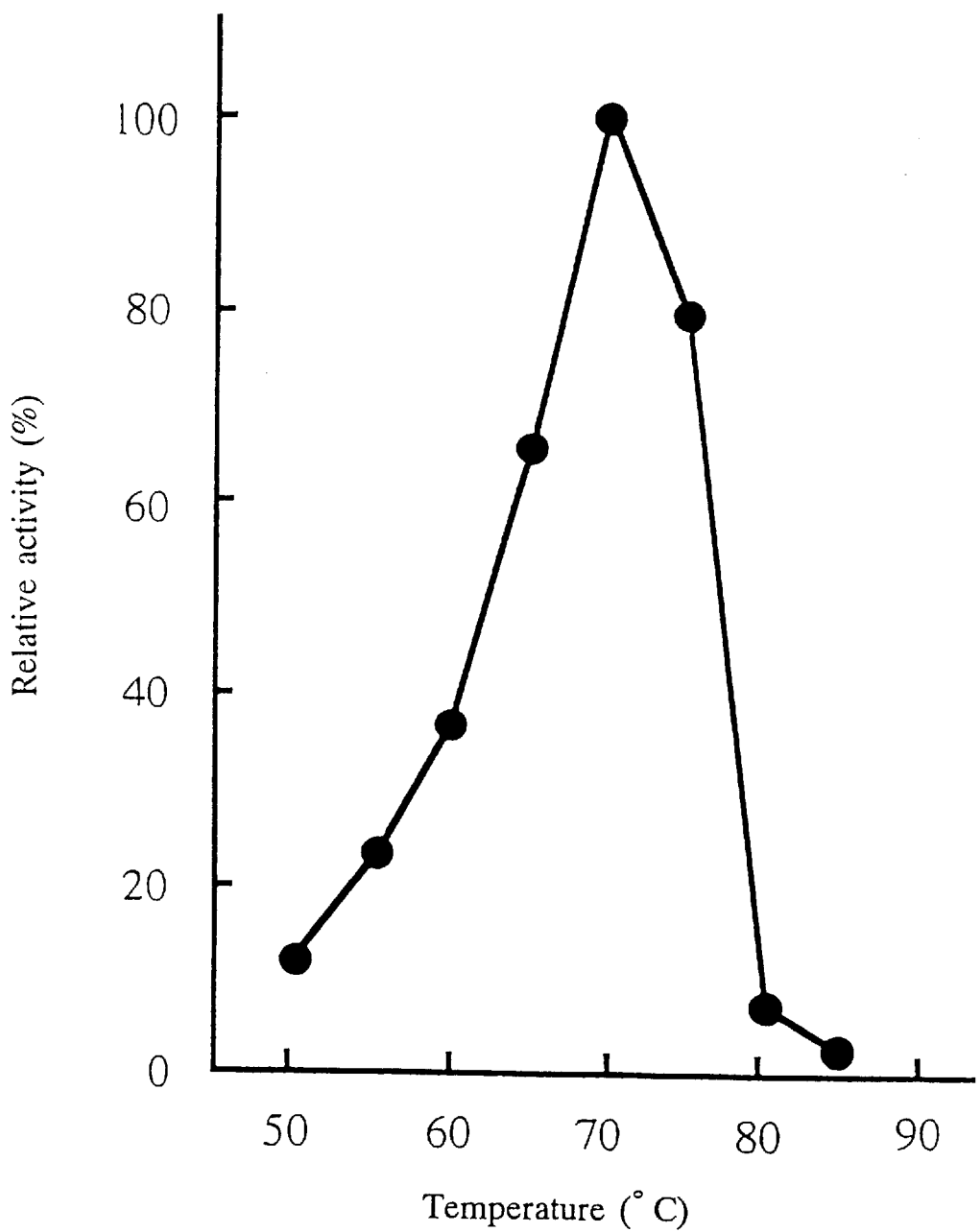
FIG. 1 shows the influence of temperatures on the activity of trehalose phosphorylase according to the present invention.

The trehalose phosphorylase according to the present invention includes enzymes which are obtainable from microorganisms of the genus Thermoanaerobium and which hydrolyze trehalose in the presence of an inorganic phosphoric acid to form D-glucose and β-D-glucose-1-phosphoric acid. The trehalose phosphorylase may have the following actions and physicochemical properties:

(1) Action
 (a) Hydrolyzing trehalose in the presence of an inorganic phosphoric acid to form D-glucose and β-D-glucose-1-phosphoric acid;
 (b) Forming trehalose and an inorganic phosphoric acid from D-glucose and β-D-glucose-1-phosphoric acid, and catalyzing the transfer reaction of glucosyl group to other saccharides using β-D-glucose-1-phosphoric acid as a saccharide donor;

(2) Molecular weight
 88,000±5,000 daltons on SDS-PAGE;

(3) Isoelectric point
 pI 5.4±0.5 on electrophoresis using ampholyte;

(4) Optimum temperature
 About 70° C. when incubated at pH 7.0 for 30 min;

(5) Optimum pH
 About 7.0–7.5 when incubated at 60° C. for 30 min;

(6) Thermal stability
 Stable up to a temperature of about 60° C. when incubated at pH 7.0 for one hour;

(7) pH Stability
 Stable at pHs of about 6.0–9.0 when incubated at 4° C. for 24 hours;

(8) Activation and stabilization
 Activated by one mM dithiothreitol; and (9) Activity inhibition Inhibited by one mM $Cu^{++}$, $Pb^{++}$, $Zn^{++}$, $Hg^{++}$, $Mg^{++}$, or $Mn^{++}$.

The trehalose phosphorylase may have the amino acid sequences of SEQ ID NO:1, SEQ ID NO:2, or SEQ ID NO:3 as a partial amino acid sequence, and as a whole, may have the amino acid sequence of SEQ ID NO:4. In this art, if there exists an isolated microorganism which produces a desired protein, functional equivalents of the protein can be easily obtained by treating the microorganism with an appropriate mutagen, or if there exists a DNA encoding a desired protein, functional equivalents of the protein can be easily obtained by applying recombinant DNA technology in general to the DNA. The present trehalose phosphorylase, of course, includes such functional equivalents. The wording "functional equivalents" means proteins which still have substantially the same activity of the trehalose phosphorylase, and have the amino acid sequence of the enzyme where one or more amino acids are replaced with different ones, one or more amino acids are either added to the N- and/or C-termini or inserted into the internal amino acid sequence, one or more amino acids in the N- and/or C-terminal regions are deleted, and one or more amino acids in the internal amino acid sequence are deleted. The present trehalose phosphorylase as mentioned above can be satisfactorily obtained by separating it from natural resources such as cultures of microorganisms which produce the enzyme, mutants thereof obtained by treating with mutagens, and artificially synthesizing the enzyme by applying recombinant DNA and peptide-synthesizing technologies.

The DNA according to the present invention includes all the above DNAs which encode the present trehalose phosphorylase. Examples of such DNAs are those which contain the amino acid sequence of SEQ ID NO:4 and encode the nucleotide sequence of SEQ ID NO:5, and functional equivalents thereof. The wording "functional equivalents" means DNAs which encode proteins, substantially have the same activity as the trehalose phosphorylase, and have the nucleotide sequence of SEQ ID NO:5 where one or more bases are replaced with different ones. In addition to the above DNAs, the present DNA includes another DNAs where the 5'- and/or 3'-termini are linked to one or more DNAs other than the above DNAs, such as start codon initiators, stop codons, Shine-Dalgarno sequence, nucleotide sequences encoding signal peptides, recognition sequences by appropriate restriction enzymes, promoters, enhancers, and terminators.

Resources and preparations of these DNAs are not specifically restricted in the present invention. For example, microorganisms of the genus Thermoanaerobium including *Thermoanaerobium brockii*, ATCC 35047, as natural resources of the DNAs, can be mentioned. DNAs containing the present DNA can be obtained by collecting DNA fractions from the cell debris of cultured microorganisms. The collected DNAs per se can be used in the present invention, and they can be prepared into an extremely favorable recombinant DNA by introducing a fragment containing the present DNA into a self-replicable vector. The recombinant DNA can be generally obtained by applying the recombinant DNA technology in general to the above DNA to obtain a gene library, and applying a selection method such as hybridization method for selecting the desired recombinant DNA from the gene library based on the nucleotide sequence, which encodes the present trehalose phosphorylase, such as SEQ ID NO:5. The recombinant DNA thus obtained can be amplified when cultured transformants obtained by introducing into appropriate hosts such as microorganisms of the genus Escherichia, followed by applying the alkali-SDS method in general to the cultures to easily obtain the present DNA in a desired amount. The present DNA can be easily obtained by applying the PCR method in a conventional manner using as a template the disrupted cells of the above microorganisms or the DNA collected from the cells, and using as a primer a DNA chemically synthesized based on SEQ ID NO:5, or by chemically synthesizing a DNA containing SEQ ID NO:5. The above functional equivalents of the present DNA can be obtained, for example, by applying the site-directed mutagenesis to the above recombinant DNA, or applying the PCR method using both the recombinant DNA as a template and a chemically synthesized DNA containing a nucleotide sequence, which was converted into the desired nucleotide sequence, as a primer.

The present DNA includes those in the form of a recombinant DNA which is introduced into a self-replicable vector. As described above, these recombinant DNAs are extremely useful in preparing the present DNA, and are also useful in producing the present trehalose phosphorylase. Once the desired DNA is obtained as described above, those recombinant DNAs can be relatively-easily obtained by applying the recombinant DNA technology in general to insert the DNA into an appropriate vector. Examples of such a vector are those which have a property of replicating in appropriate hosts. The following vectors can be arbitrarily used in the present invention; pUC18, Bluescript® II SK(+), pKK223-3, and λgt·λC which require microorganisms of the genus Escherichia as hosts; pUB110, pTZ4, pC194, ρ11, φ1, and φ105 which require microorganisms of the genus Bacillus as hosts; and pHY300PLK, pHV14, TRp7, YEp7, and pBS7 which require at least two types of hosts. Referring to an example of method for inserting the present DNA into the vectors, an appropriate vector and either the present DNA thus obtained or a DNA containing the present DNA are cleaved with a restriction enzyme, and the formed DNA fragments and vector fragments are ligated. Examples of such a restriction enzyme suitably used are Acc I, Alu I, Bam HI, Bgl II, Bst XI, Eco RI, Hind III, Not I, Pst I, Sac I, Sal I, Sma I, Spe I, Xba I, and Xho I. In the case of ligating the DNA and vector fragments, for example, chemically synthesized DNAs, having appropriate recognition sequences for the restriction enzymes, can be used. To ligate DNAs with others they are contacted with DNA ligases intra- and extra-cellularly after annealing.

The present DNA includes those in the form of a transformant into which the DNA is introduced. Such a transformant is extremely usable to obtain the present trehalose phosphorylase and DNA. For example, microorganisms of the genera Escherichia and Bacillus, actinomyces, and yeasts can be arbitrarily used as host microorganisms for the transformant. The transformant can be usually obtained by introducing the aforesaid recombinant DNA into an appropriate host; when used a microorganism of the genus Escherichia, the microorganism and the recombinant DNA are cultured in the presence of calcium ion, while the competent cell and protoplast methods are applied when used a microorganism of the genus Bacillus. The aforesaid methods for preparing the present DNA are in themselves conventional ones used in the art as described, for example, by J. Sumbruck et al. in "*Molecular Cloning A Laboratory Manual*", 2nd edition, published by Cold Spring Harbor Laboratory Press (1989).

The present process for producing trehalose phosphorylase is characterized in that it comprises culturing microorganisms which produce the present enzyme, and collecting the produced enzyme from the cultures. The genus and species of such microorganisms and cultivation methods used in the present invention are not specifically restricted. Examples of such microorganisms include those which belong to the genus Thermoanaerobium, preferably, *Thermoanaerobium brockii*, ATCC 35047, and transformants obtained by introducing the present DNA into appropriate host microorganisms.

Any natural- and synthetic-nutrient culture media can be used for culturing the microorganisms used in the present invention as long as the microorganisms can grow therein and produce the present enzyme. The carbon sources used in the present invention are those which can be utilized by the microorganisms; for example, saccharides such as maltose, trehalose, dextrins, and starches, and natural substances which contain saccharides such as molasses and yeast extracts can be used. The concentration of these carbon sources contained in the culture media is chosen depending on their types. For example, preferable saccharide concentrations are not higher than 20 w/v %, and not higher than 5 w/v % with respect to the microorganisms' growth and proliferation. The nitrogen sources used in the present invention are, for example, inorganic nitrogen-containing compounds such as ammonium salts and nitrates, and organic nitrogen-containing compounds such as urea, corn steep liquor, casein, peptone, yeast extract, and meet extract. If necessary, inorganic compounds, for example, salts of calcium, magnesium, potassium, sodium, phosphoric acid, manganese, zinc, iron, copper, molybdenum, and cobalt can be used in the present invention.

The microorganisms are anaerobically cultured under the conditions selected from at temperatures of 50°–80° C., preferably, 60°–70° C., and at pHs of 5–8, preferably, 6.5–7.5. Any cultivation time can be used in the present invention as long as it is sufficient for the growth of the microorganisms, preferably, 10–50 hours. For the culture of the above transformants, they are generally cultured at temperatures of 20°–65° C. and pHs of 2–9 for about 1–6 days under aerobic conditions by aeration-agitation method.

After culturing the microorganisms, the present enzyme can be collected from the cultures. Because the enzyme activity may be generally present intracellularly, intact and processed cells can be obtained as crude enzymes. Whole cultures can be also used as crude enzymes. Conventional solid-liquid separation methods can be used to separate cells and nutrient culture media; for example, methods to directly centrifuge the cultures, those to filtrate the cultures after adding filer aids to the cultures or after pre-coating, and those to filter the cultures using membranes such as plain filters and hollow fibers can be used. The intact and processed cells per se can be used as crude enzymes, and if necessary, they can be prepared into partially purified enzymes.

The types of the processed cells include protein fractions of cells, immobilized preparations of intact and processed cells, and cells which were dried, lyophilized, and treated with surfactants, enzymes, ultrasonication, mechanical grinding, and mechanical pressure. The present enzyme can be used in a crude or purified form, and the processed cells can be usually further treated with conventional methods used for purifying enzymes, for example, salting out using ammonium sulfate, sedimentation using acetone and alcohol, and membrane concentration/dialysis using plain membranes and hollow fibers.

The intact and processed cells can be immobilized by conventional methods; for example, binding methods with ion exchangers, covalent bonding/adsorption methods with resins and membranes, and inclusion methods using high molecular substances.

The crude enzymes can be used intact or may be purified by conventional purification methods. For example, the processed cells are salted out using ammonium sulfate into crude enzymes, followed by dialyzing the enzymes and treating them successively with anion exchange column chromatography using "DEAE-TOYOPEARL®", a cation exchanger commercialized by Tosoh Corporation, Tokyo, Japan, anion exchange column chromatography using "CM-TOYOPEARL®" a resin commercialized by Tosoh Corporation, a hydrophobic column chromatography using "BUTYL-TOYOPEARL®", a hydrophobic resin commercialized by Tosoh Corporation, Tokyo, Japan, and gel filtration column chromatography using "ULTROGEL® AcA44 RESIN", a gel for gel filtration column chromatography commercialized by Sepracor/IBF s.a. Villeneuve la Garenne, France, to obtain an electrophoretically single protein band of enzyme.

The present trehalose phosphorylase activity is assayed as follows: Add 0.2 ml of an enzyme solution to 2 ml of 20 mM phosphate buffer (pH 7.0) containing 1.0 w/v % trehalose as a substrate, incubate the solution at 60° C. for 30 min, sample the reaction mixture in an amount of 0.5 ml, and incubate the sample at 100° C. for 10 min to suspend the enzymatic reaction. Add 0.5 ml of D-glucose oxidase/peroxidase reagent to the heated sample, stir the mixture, keep the mixture at 40° C. for 30 min, add 2.5 ml of 5-N hydrochloric acid, stir the resulting mixture, and measure the absorbance of the mixture at a wavelength of 525 nm. One unit of the enzyme activity is defined as the enzyme that forms one pmole of D-glucose per one minute. The activity of maltose- and kojibiose-phosphorylases can be assayed similarly as the same assay as indicated above except that the trehalose as a substrate is respectively replaced with maltose and kojibiose.

In the present enzymatic reaction using the trehalose phosphorylase to produce saccharide compositions containing glucosyl-transferred saccharides, the enzyme is generally allowed to contact with β-D-glucose-1-phosphoric acid as a saccharide donor along with other appropriate saccharides as acceptors, for example, monosaccharides such as D-xylose, D-galactose, G-glucose, D-fucose, and L-fucose to transform glucosyl group to the above reducing saccharides, resulting in a formation of glucosyl-D-xyloside, glucosyl-D-galactoside, trehalose, glucosyl-D-fucoside, and glucosyl-L-fucoside, respectively.

Commercially available β-D-glucose-1-phosphoric acid as a reagent can be used intact as a saccharide donor in the present invention, and it can be prepared by contacting an appropriate phosphorylase with a saccharide as a substrate in the presence of an inorganic phosphoric acid and/or its salt; for example, it can be prepared by, in the presence of an inorganic phosphoric acid and/or its salt, contacting trehalose phosphorylase with trehalose, contacting maltose with maltose phosphorylase, or contacting kojibiose with kojibiose phosphorylase. When either of the above reactions of the phosphorylases that form β-D-glucose-1-phosphoric acid is conducted in the same reaction system using the present trehalose phosphorylase to form glucosyl-transferred saccharides, it can directly supply β-D-glucose-1-phosphoric acid to the system, resulting in a reduction of the production costs and a simplification of the production steps as advantageous features. The inorganic phosphoric acid as mentioned above includes orthophosphoric acid and condensed phosphoric acid, and usually, the former acid is preferably used. The salt of inorganic phosphoric acid includes compounds of phosphoric ion in general, derived from the above inorganic phosphoric acid, and usually, highly-water soluble sodium- and potassium-salts of phosphoric acid are preferably used.

For example, the present enzyme can be used as the above trehalose phosphorylase, and commercially available bacterial maltose phosphorylases can be used as such. For the kojibiose phosphorylase, it can be used the enzyme disclosed in Japanese Patent Application No.311,235/96, applied by the same applicant of the present invention, entitled "*Kojibiose phosphorylase, its preparation and uses*". Detailed descriptions were in the specification; for example, a seed culture of *Thermoanaerobium brockii*, ATCC 35047, was inoculated into the nutrient culture medium for the microorganism as described in "*ATCC Catalogue of BACTERIA AND BACTERIOPHAGES*", 18th edition, pp.452–456 (1992), and cultured in the medium at 65° C. under anaerobic conditions, followed by centrifuging the culture, disrupting the cells with ultrasonics, and collecting the resulting supernatant to obtain the desired fraction with kojibiose phosphorylase activity.

The substrate concentration used in the glucosyl-transferred saccharide formation reaction using the present trehalose phosphorylase is not specifically restricted. Generally, preferably used are solutions containing 1–20 w/w % (the wording "w/w %" will be abbreviated as "%" throughout the specification, unless specified otherwise) of β-D-glucose-1-phosphoric acid as a saccharide donor and 1–20% of an acceptor. As described above, when the β-D-glucose-1-phosphoric acid formation reaction by the action of an appropriate phosphorylase is conducted in the same reaction system of the above glucosyl-transferred saccharide-forming reaction, the followings are recommendable: When contacting trehalose phosphorylase with its substrates, about 1–20% trehalose solutions are used in place of β-D-glucose-1-phosphoric acid as a substrate of the glucosyl-transferring reaction in the presence of about 0.5–20 mM of phosphates such as sodium dihydrogenphosphate. When contacting other phosphorylases with their substrates, about 1–20% maltose or kojibiose can be coexisted along with about 0.5–20 mM of phosphates such as sodium dihydrogenphosphate in place of the β-D-glucose-1-phosphoric acid as a substrate for the glucosyl-transferring reaction. Depending on the type of saccharides used, either maltose- or kojibiose-phosphorylase can be preferably coexisted in an amount of about 0.1–50 units/g saccharide, on a dry solid basis (d.s.b.).

The above reaction can be carried out at temperatures that do not inactivate the enzymes used in the presence of the substrates, i.e. up to about 70° C., preferably, about 15°–65° C. The reaction pH can be usually adjusted to pHs of about 4.0–9.0, preferably, about 5.0–7.5. The reaction time can be appropriately chosen depending on the enzymatic reaction rates, usually, it is about 0.1–100 hours when the enzymes are usually used in an amount of about 0.1–50 units/g substrate, d.s.b. As described above, when the β-D-glucose-1-phosphoric acid formation reaction by the action of different phosphorylases is conducted in the same reaction system of the glucosyl-transferred saccharide-forming reaction, the reaction temperatures and pHs are preferably set to those which do not inactivate the phosphorylases used depending on their thermal stabilities.

Thus, the resulting reaction mixtures contain glucosyl-transferred saccharides which correspond to the saccharides used as substrates. The yields of glucosyl-transferred saccharides are varied depending on the substrate concentrations, types of substrates, and reaction conditions used in the enzymatic reactions. For example, in the case of using 10% trehalose and 5% D-galactose are used as substrates in the presence of an inorganic phosphoric acid, glucosylgalactoside is formed in a yield of about 30%. Throughout the specification, the yields of glucosyl-transferred saccharides mean their percentages (%) of the formed saccharides to the total saccharides in reaction mixtures, d.s.b.

To increase the content of glucosyl-transferred saccharides in the reaction mixtures to the highest possible level, enzyme sources, which decompose and remove D-glucose formed in the reaction mixtures, can be advantageously coexisted in the mixtures to promote the saccharide-transferring reactions. Such a technique can be satisfactorily used to decompose and remove D-glucose as a by-product formed during the reaction processes and to promote the saccharide-transferring reaction when the above β-D-glucose-1-phosphoric acid formation reaction using an appropriate phosphorylase is carried out in the same reaction system of the glucosyl-transferring reaction to directly supply saccharide donors.

The enzyme sources are microorganisms which have a D-glucose decomposing activity, cultures of such microorganisms, their intact and processed cells, and enzymes with a D-glucose decomposing activity. Any microorganisms can be used as long as they have a relatively-high D-glucose decomposing activity but have no or substantially no activity of decomposing the formed transferred saccharides; preferable ones are yeasts. Any enzymes such as glucose oxidase, catalase, pyranose oxidase, glucose dehydrogenase, glucokinase, and hexokinase can be used. Among these enzymes, the glucose oxidase and catalase can be preferably used.

The reaction mixtures containing the glucosyl-transferred saccharides thus produced can be in a conventional manner filtered and centrifuged to remove impurities, then subjected to purification steps such as decoloration with activated charcoals, and desalting with ion exchangers in H- and OH-form, and concentrated into syrupy products. If necessary, the syrupy products can be arbitrarily dried by spray drying, etc., into powdery products.

The present saccharide compositions containing glucosyl-transferred saccharides can be processed into products rich in the saccharides by separating the saccharides from reaction mixtures and purifying the resulting mixtures. Examples of such separation methods are those which separate and remove impurities; fermentation methods using yeasts to remove monosaccharides or yeast fermentation methods, and methods to remove concomitant saccharides such as membrane filtrations, column chromatographies, and methods comprising adjusting the reaction mixtures to alkaline pHs, and heating the mixtures to decompose reducing saccharides. More particularly, advantageously used on an industrial scale are methods for removing concomitant saccharides to collect fractions rich in the desired glucosyl-transferred saccharides by removing concomitant saccharides on column chromatographies using strong-acid cation exchange resins as disclosed in Japanese Patent Kokai Nos.23,799/83 and 72,598/83. In this case, conventional fixed-bed, moving-bed, and semi-moving methods can be arbitrarily used.

The solutions separated from impurities can be in a conventional manner filtered and centrifuged to remove insoluble substances, subjected to purification steps such as decoloration with activated charcoals, and desalting with ion exchange resins in H- and OH-form, and concentrated into syrupy products. If necessary, the syrupy products can be dried by methods such as spray drying into powdery products.

The present saccharide compositions containing glucosyl-transferred saccharides thus obtained usually contain at least 5%, preferably, at least 10% of the glucosyl-transferred saccharides, d.s.b.

The present saccharide compositions containing glucosyl-transferred saccharides have a satisfactory taste and sweetness, osmosis-controlling ability, humectancy, gloss-imparting ability, crystallization-preventing ability, and retrogradation-preventing ability, anti-cariosity, growth-promoting activity for bifid bacteria, and mineral-absorption-promoting activity. Because of these satisfactory properties and functions, the present saccharide compositions can be arbitrarily used widely in compositions such as food products, tobaccos, cigarettes, feeds, pet foods, cosmetics, pharmaceuticals, shaped bodies, daily foods and products, products of forestry and fisheries, reagents, and products for chemical industries.

The present saccharide compositions containing glucosyl-transferred saccharides can be used intact as a seasoning for sweetening. If necessary, the present saccharide compositions can be used together with adequate amounts of one or more other sweeteners, for example, powdered syrup, glucose, maltose, trehalose, sucrose, isomerized sugar, honey, maple sugar, sorbitol, maltitol, lactitol, dihydrocharcone, stevioside, $\alpha$-glycosyl stevioside, rebaudioside, glycyrrhizin, L-aspartyl-L-phenylalanine methyl ester, saccharin, glycine, and alanine, as well as fillers such as dextrins, starches, and lactose.

The present saccharide compositions have a sweetness which well harmonizes with substances having sourness, acidity, saltiness, bitterness, astringency, and deliciousness, as well as a satisfactory acid- and heat-tolerance. Thus, they can be arbitrarily used in food products in general as a sweetener, taste-improving agent, and quality-improving agent.

The present saccharide compositions can be used in seasonings such as soy sauces, powdered soy sauces, "miso", "funmatsu-miso" (a powdered miso), "moromi" (a refined sake), "hishio" (a refined soy sauce), "furikake" (a seasoned fish meal), mayonnaise, dressings, vinegars, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauces, catsups, premixes for pickles and pickled products such as "takuan-zuke-no-moto" (a premix for pickled radish), and "hakusai-zuke-no-moto" (a premix for fresh white rape pickles), "yakiniku-no-tare" (a sauce for Japanese grilled meat), curry roux, instant stew mixes, instant soup mixes, "dashi-no-moto" (an instant stock mix), mixed seasonings, "mirin" (a sweet sake), "shin-mirin" (a synthetic mirin), table syrups, and coffee syrups.

The present saccharide composition can be freely used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jellies, pao de Castellas and "amedama" (a Japanese toffee); confectioneries such as buns, biscuits, crackers, cookie, pies, puddings, butter creams, custard creams, cream puffs, waffles, sponge cakes, doughnuts, chocolates, chewing gums, caramels and candies; frozen desserts such as ice creams and sherbets; syrups such as "kajitsu-no-syrup-zuke" (a preserved fruit), and "korimitsu" (a sugar syrup for shaved ice); pastes such as flour pastes, peanut pastes, fruit pastes, and spreads; processed fruits and vegetables such as jams, marmalades, "syrup-zuke" (fruit pickles), and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); meat products such as hams and sausages; products of fish meats such as fish hams, fish sausages, "kamaboko" (a steamed fish paste), "chikuwa" (a kind of fish paste), and "tenpura" (a Japanese deep-fat fried fish paste); "chinmi" (a relish) such as "uni-no-shiokara" (salted guts of sea urchin), "ika-no-shiokara" (salted guts of squid), "su-konbu" (processed tangle), "saki-surume" (dried squid strips), and "fugu-no-mirin-boshi" (a dried mirin-seasoned swellfish); "tsukudani" (a food boiled down in soy sauce) such as those of lavers, edible wild plants, dried squids, fishes, and shell-fishes; daily dishes such as "nimame" (cooked beans), potato salads, and "konbu-maki" (a tangle roll); milk products; canned and bottled products such as those of meats, fish meats, fruits, and vegetables; alcoholic beverages such as sakes, synthetic sakes, wines and liquors; soft drinks such as coffees, teas, cocoas, juices, carbonated beverages, sour milk beverages, and beverages containing lactic acid bacteria; instant food products such as instant pudding mixes, instant hot cake mixes, and "sokuseki-shiruko" (an instant mix of adzuki-bean soup with rice cake), and instant soup mixes; and foods such as baby foods, foods for therapy, beverages supplemented with nutritions, cooked rice products, noodles, and frozen foods; as well as for improving the tastes and qualities of the above food products.

The present saccharide compositions can be also used in feeds and pet foods for animals such as domestic animals, poultry, and fishes to improve their taste preferences. The present saccharide compositions can be arbitrarily used as a sweetener, taste-improving agent, and quality-improving agent in other compositions in a paste and liquid form such as tobaccos, cigarettes, dentifrices, lipsticks, rouges, lip creams, internal medicines, tablets, troches, cod liver oils in the form of drops, cachous, oral refrigerants, gargles, cosmetics, and pharmaceuticals.

The present saccharide compositions can be used as a quality-improving agent and stabilizer in biologically active substances susceptible to lose their effective ingredients and activities, as well as in health foods and pharmaceuticals containing the above biologically active substances. Examples of such biologically active substances are solutions of cytokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor, and interleukins 1, 2, 6, 12, 15 and 18; hormones such as insulin, growth hormone, prolactin, erythropoietin, tissue plasminogen activator, follicle-stimulating hormone, and placental hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; vitamins such as thiamine, riboflavin, L-ascorbic acid, cod liver oil, carotenoid, ergosterol, and tocopherol; enzymes such as lipase, elastase, urokinase, protease, $\beta$-amylase, isoamylase, glucanase, and lactase; extracts such as ginseng extract, snapping turtle extract, chlorella extract, aloe extract, and propolis extract;

viable microorganisms such as viruses, lactic acid bacteria, and yeasts; and other biologically active substances such as royal jelly. By using the present saccharide compositions, the aforementioned biologically active substances are arbitrary prepared into health foods and pharmaceuticals with a satisfactorily-high stability and quality without fear of losing or inactivating their effective ingredients and activities.

As described above, the wording "compositions" as referred to in the present invention include orally- and parenterally-usable food products, cosmetics, and pharmaceuticals, as well as daily products, products of forestry and fisheries, reagents, and products for chemical industries.

Methods to incorporate the present saccharide compositions into the above compositions include conventional methods, for example, mixing, kneading, dissolving, melting, soaking, permeating, sprinkling, applying, coating, spraying, injecting, and solidifying. The present saccharide composition is usually incorporated into the compositions in an amount of 0.1% or more, preferably, 0.5% or more.

The following experiments explain the present invention in more detail:

Experiment 1

Preparation of Trehalose Phosphorylase

According to the preparation of the medium for *Thermoanaerobium brockii* as disclosed in "*ATCC Catalogue of BACTERIA AND BACTERIOPHAGES*", 18th edition, pp.452–456 (1992), except for replacing 0.5 w/v % glucose with 0.5 w/v % trehalose as a carbon source, a medium was prepared, and 100 ml aliquots of the medium were placed in 100-ml pressure bottles, followed by inoculating a seed of *Thermoanaerobium brockii*, ATCC 35047, and allowing to stand at 60° C. for 48 hours for a seed culture.

About 10 L aliquots of a fresh preparation of the same nutrient culture medium as used for preparing the seed culture were placed in four 11-l stainless steel bottles, sterilized by heating, cooled to 60° C., and inoculated with one v/v % of the seed culture to the culture medium, followed by the stationary culture at 60° C. for about 40 hours.

About 40 L of the resultant pooled cultures were centrifuged to obtain 92 g wet cells which were then suspended in 10 mM phosphate buffer, ultrasonicated, and centrifuged to obtain a supernatant of the disrupted cell suspension. The supernatant had an activity of 0.3 unit/ml of trehalose phosphorylase.

Experiment 2

Purification of Trehalose Phosphorylase

The supernatant in Experiment 1 was concentrated using a UF membrane into an about 360 ml of enzyme concentrate having an activity of about 30 units/ml of trehalose phosphorylase.

Three hundred ml of the enzyme concentrate was dialyzed against 10 mM phosphate buffer (pH 7.0) for 24 hours, and centrifuged to remove insoluble substances. Three hundred and eighty ml of the resulting supernatant was subjected to ion exchange column chromatography using 380 ml of "DEAE-TOYOPEARL® 650 GEL", a gel for ion exchange column chromatography commercialized by Tosoh Corporation, Tokyo, Japan.

The present trehalose phosphorylase was allowed to be adsorbed on the gel, and eluted from the column by feeding a linear gradient of sodium chloride increasing from 0M to 0.5M. Fractions with the enzyme activity, eluted at about 0.1M sodium chloride, were collected and pooled, and the enzyme in the pooled solution was then purified as follows: Dialyze the solution against a fresh preparation of the same buffer containing 1.5M ammonium sulfate, centrifuge the dialyzed solution to remove insoluble substances, and subject the supernatant to hydrophobic column chromatography using 100 ml of "BUTYL-TOYOPEARL® 650 GEL". Elute the trehalose phosphorylase adsorbed on the gel with a linear gradient of ammonium sulfate decreasing from 1.5M to 0.5M, and collect fractions with the enzyme activity.

The fractions were pooled and subjected to gel filtration chromatography using 300 ml of "ULTROGEL® AcA44 RESIN", a gel for gel filtration column chromatography commercialized by Sepracor/IBF s.a. Villeneuve la Garenne, France, followed by collecting fractions with the enzyme activity.

The yield of the purified enzyme specimen, obtained by the above purification steps, was about 25% with respect to the enzyme activity of the supernatant of the disrupted cell suspension. The enzyme specimen had a specific activity of 78.2 units/mg protein. Protein was quantified according to the Lowry method using calf serum albumin as a standard protein.

Examination for the purity of the specimen on gel electrophoresis using 7.5 w/v % polyacrylamide revealed that the specimen was a relatively-high purity protein detected as a single protein band.

Experiment 3

Property of Trehalose Phosphorylase

The trehalose phosphorylase specimen in Experiment 2 was subjected to SDS-PAGE using 10 w/v % gel. Comparing with marker proteins, commercialized by Japan Bio-Rad Laboratories, Tokyo, Japan, which were electrophoresed in parallel, the molecular weight of the enzyme was measured, revealing that it had a molecular weight of 88,000±5,000 daltons and gave a molecular weight of 190,000±10,000 daltons on gel filtration using a column, 7.5 mm in diameter and 600 mm in length, packed with "TSKgel G4000SW", a gel for gel filtration commercialized by Tosoh Corporation, Tokyo, Japan.

The purified trehalose phosphorylase was subjected to polyacrylamide gel electrophoresis using 2 w/v % "AMPHOLINE", an ampholyte commercialized by Pharmacia LKB Biotechnology AB, Uppsala, Sweden, followed by measuring the pHs of protein bands and gels, revealing that the enzyme had a pI of 5.4±0.5.

Figure 2:
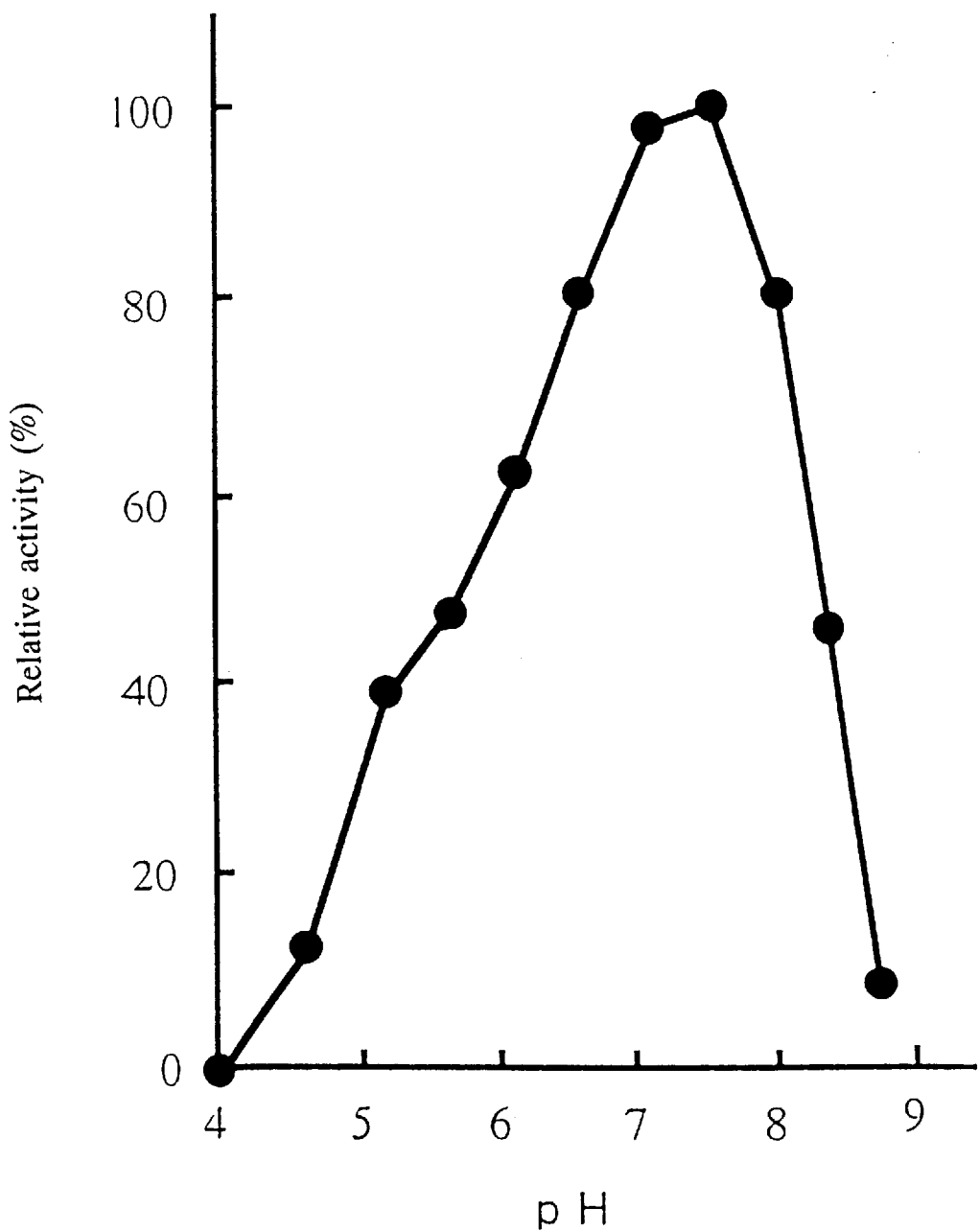
FIG. 2 shows the influence of pHs on the activity of trehalose phosphorylase according to the present invention.
Figure 3:
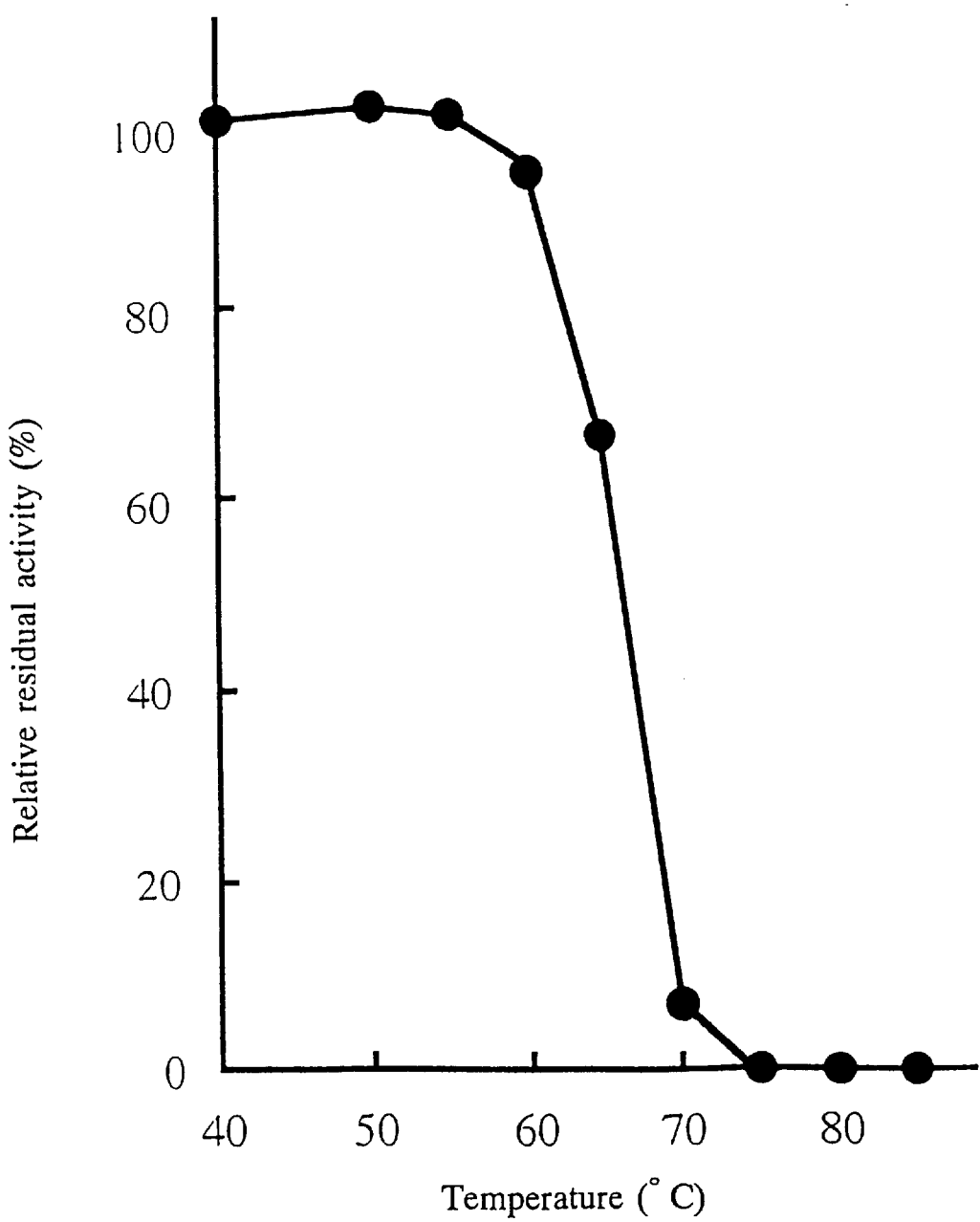
FIG. 3 shows the influence of temperatures on the stability of trehalose phosphorylase according to the present invention.
Figure 4:
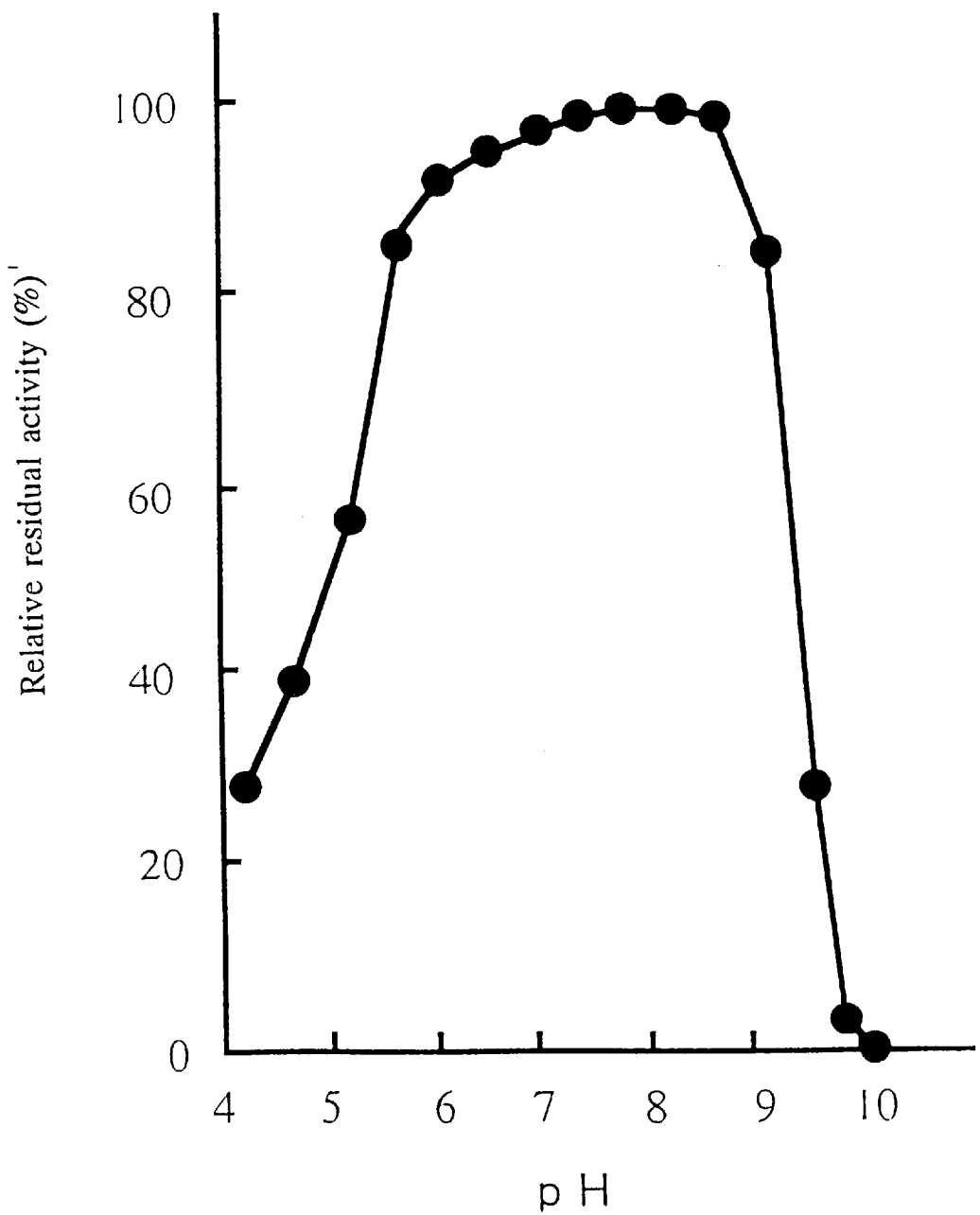
FIG. 4 shows the influence of pHs on the stability of trehalose phosphorylase according to the present invention.

Influences of temperatures and pHs on the present trehalose phosphorylase activity were studied in accordance with the assay for enzyme activity. To study the influence of temperatures, the enzyme was reacted at temperatures of about 50°–85° C. in place of 60° C. as used in the enzyme assay. In the case of studying the influence of pHs, the enzyme was reacted at pHs of about 4–9 in place of the buffer's pH as used in the assay for the enzyme activity. In both cases, the enzymatic reactions were suspended similarly as in the enzyme assay, followed by quantifying the formed glucose. These results were in FIGS. 1 and 2 which were respectively the data for influences of temperatures and pHs, and expressed by relative values to the maxima. The enzyme had an optimum temperature of about 70° C. when incubated at pH 7.0 for 30 min, and the optimum pH was about 7.0–7.5 when incubated at 60° C. for 30 min. The thermal stability of the enzyme was determined by incubating the enzyme dissolved in 10 mM phosphate buffer (pH 7.0) at a temperature of about 40°–85° C. for one hour, cooling the incubated enzyme, and assaying for the residual enzyme activity according to the enzyme assay. The pH stability of the enzyme was determined by dissolving the enzyme in buffers with different pHs of about 4–10, keeping each enzyme solution at 4° C. for 24 hours, adjusting each solution to give a pH of 7.0, and assaying for the residual enzyme activity according to the enzyme assay. These results were in FIGS. 3 and 4 which were respectively the data for thermal and pH stabilities of the enzyme and expressed by relative values to the maxima. The enzyme had a thermal stability of up to about 60° C. and a pH stability of about 6.0–9.0. The enzyme activity was inhibited by one mM $Cu^{++}$, $Pb^{++}$, $Zn^{++}$, $Hg^{++}$, $Mg^{++}$, or $Mn^{++}$.

Experiment 4

Partial Amino Acid Sequence of Trehalose Phosphorylase

Experiment 4-(1)

N-Terminal Amino Acid Sequence

A portion of a purified enzyme specimen, obtained by the method in Experiment 2, was dialyzed against distilled water, and about 40 μg of the dialyzed enzyme by protein weight was used as a sample for analyzing the N-terminal amino acid sequence. "PROTEIN SEQUENCER MODEL 473A", an apparatus commercialized by Applied Biosystems, Inc., Foster City, USA, was used to analyze up to five amino acid resides from the N-terminus. The analyzed partial amino acid sequence was SEQ ID NO:1. More precise analysis using a fresh preparation of the same enzyme specimen revealed that the enzyme has the amino acid sequence of SEQ ID NO:6 at the N-terminus.

Experiment 4-(2)

Internal Partial Amino Acid Sequence

A portion of a purified enzyme specimen, obtained by the method in Experiment 2, was dialyzed against 10 mM Tris-HCl buffer (pH 9.0), and the dialyzed solution was diluted with a fresh preparation of the same buffer to give a protein concentration of one mg/ml. One ml of the resulting solution was admixed with 10 μg of lysyl endopeptidase, an enzyme specimen commercialized by Wako Pure Chemical Industries, Ltd., Tokyo, Japan, and subjected to an enzymatic reaction at 30° C. for 22 hours to form peptides. Reversed phase HPLC (high-performance liquid chromatography) was performed to isolate the peptides under the conditions of using "μBONDASPHERE C-18 COLUMN (2.1 mm in diameter and 150 mm in length)", a column for reversed phase HPLC commercialized by Waters Chromatography, Div., MILLIPORE Corp., Milford, Mass., USA, flow rate of 0.9 ml/min, ambient temperature, and a linear gradient of acetonitrile increasing from 0 v/v % to 48 v/v % in 0.1 v/v % trifluoroacetic acid over 120 min. Peptides eluted from the column were detected by measuring their absorbances at 210 nm. Two peptides, i.e., TP10 with a retention time of 66 min and TP14 with a retention time of 86 min, which were clearly separated from others, were separately collected, dried in vacuo, and dissolved in 200 μl of a solution of 0.1 v/v % trifluoroacetic acid and 50 v/v % acetonitrile. Each peptide was analyzed on a protein sequencer to reveal up to five amino acid residues from the N-terminus. The TP10 and TP14 gave the amino acid sequences of SEQ ID NO:2 and SEQ ID NO:3, respectively. More precise analysis of a fresh preparation of the same enzyme specimen by the same analysis revealed that the TP14 has SEQ ID NO:7 at the N-terminus.

Experiment 5

Substrate Specificity for Saccharide-hydrolyzing Reaction by Trehalose Phosphorylase An aqueous solution of a saccharide selected from D-glucose, maltose, sucrose, lactose, trehalose, neotrehalose, cellobiose, melibiose, kojibiose, isomaltose, sophorose, gentibiose, nigerose, laminaribiose, maltopentaose, and 4-O-α-D-glucosyltrehalose was mixed with 10 units/g saccharide, d.s.b., of a purified trehalose phosphorylase obtained by the method in Experiment 2, and incubated in the presence of 5 mM disodium hydrogenphosphate at 60° C. and pH 7.0 for 24 hours. The saccharide concentration of each reaction solution was 2 w/v %. Pre-reaction solutions and post-reaction mixtures were subjected to thin layer chromatography (hereinafter abbreviated as "TLC") using "KIESELGEL 60 (20×20 cm)", an aluminum plate for TLC commercialized by Merck & Co., Inc., Rahway, USA. Samples were developed once at ambient temperature on the plate using 1-butanol/pyridine/water (=7:3:1 by volume) as a developing solvent system, and the plate was sprayed with 20 v/v % sulfuric acid/methanol solution, and heated at 110° C. for about 10 min for coloration. Comparing spots of the solutions and mixtures detected on the plates, it was checked whether the enzyme acted on the saccharides. The results were in Table 1:

TABLE 1

| Substrate | Decomposition |
| --- | --- |
| D-Glucose | − |
| Maltose | − |
| Sucrose | − |
| Lactose | − |
| Trehalose | + |
| Neotrehalose | − |
| Cellobiose | − |
| Melibiose | − |
| Kojibiose | − |
| Isomaltose | − |
| Sophorose | − |
| Gentibiose | − |
| Nigerose | − |
| Laminaribiose | − |
| Maltopentaose | − |
| 4-O-α-D-glucosyltrehalose | − |

Note)
+: Hydrolyzed by the action of the present trehalose phosphorylase.
−: Not hydrolyzed by the action of the present trehalose phosphorylase.

As shown in Table 1, it was found that the present trehalose phosphorylase showed a strong substrate specificity to trehalose and acted on it to form D-glucose and β-D-glucose-1-phosphoric acid, but did not act on other saccharides.

Experiment 6

Specificity to Acceptor in Glucosyl-transferring Saccharide-forming Reaction by Trehalose Phosphorylase An aqueous solution, which dissolved in an equal amount, by dry weight, of β-D-glucose-1-phosphoric acid as a saccharide donor and one of the monosaccharides, oligosaccharides, and sugar alcohols as acceptors in Table 2, was admixed with 10 units/g β-D-glucose-1-phosphoric acid of a purified trehalose phosphorylase obtained by the method in Experiment 2, and enzymatically reacted at 60° C. and pH 7.0 for 24 hours. Similarly as in Experiment 5, the pre-reaction solutions and the post-reaction mixtures were subjected to TLC, followed by coloring the plates. Comparing spots of the samples of the solutions and mixtures detected on the plates, it was judged whether transferred saccharides were formed based on newly detected spots of the post reaction mixtures. By macroscopically observing the coloration degree of the newly detected spots, the yield of the transferred saccharides was relatively evaluated. The results were in Table 2:

TABLE 2

| Acceptor | | Formation of glucosyl- |
| --- | --- | --- |
| Classification | Name | transferred saccharide |
| Aldopentose | D-Xylose | +++ |
| | L-Xylose | − |
| | D-Ribose | − |
| Aldohexose | D-Galactose | ++ |
| | D-Glucose | +++ |
| | D-Mannose | + |
| Ketohexose | L-Sorbose | − |
| | D-Fructose | − |
| Deoxysugar | 2-Deoxyglucose | ++ |
| | D-Fucose | +++ |
| | L-Fucose | +++ |
| Glucoside | α-Methyl glucoside | − |
| | β-Methyl glucoside | − |
| Sugar alcohol | Sorbitol | − |
| Amino sugar | Glucosamine | ++ |
| | N-Acetyl glucosamine | ++ |
| Disaccharide | Maltose | − |
| | Lactose | − |
| | Isomaltose | − |
| | Cellobiose | − |
| | Sucrose | − |

Note)
−: No glucosyl-transferred saccharide formed.
+: Glucosyl-transferred saccharide was formed in a relatively-small amount.
++: Glucosyl-transferred saccharide was formed in a relatively-large amount.
+++: Glucosyl-transferred saccharide was formed in a considerably-large amount.

As shown in Table 2, it was revealed that the present trehalose phosphorylase forms glucosyl-transferred saccharides by effectively transferring glucosyl group from β-D-glucose-1-phosphoric acid as a saccharide donor to reducing aldoses as acceptors such as monosaccharides such as D-xylose, D-galactose, D-glucose, 2-deoxy-D-glucose, D-fucose, L-fucose, glucosamine, and N-acetyl glucosamine. Considering the substrate specificity of the present enzyme, these glucosyl-transferred saccharides were judged to be non-reducing saccharides. No glucosyl-transferred saccharide was obtained when α-D-glucose-1-phosphoric acid was used as a saccharide donor in place of β-D-glucose-1-phosphoric acid.

Some of the glucosyl-transferred saccharides, which were revealed in Experiment 6 to be formed via the saccharide-transferring reaction by the present trehalose phosphorylase, will be explained on their detailed structures with reference to the following Experiments 7 and 8.

Experiment 7

Glucosyl-transferred Saccharide from D-glucose and β-D-glucose-1-phosphoric Acid A portion of the reaction mixture, obtained by using as substrates D-glucose and β-D-glucose-1-phosphoric acid in Experiment 6, was diluted with 10 mM phosphate buffer (pH 7.0) to give a concentration of one percent, admixed with 0.5 ml of a trehalase specimen commercialized by Sigma Chemical Company, St. Louis, USA, and enzymatically reacted at 45° C. for 20 hours. Each portion of the reaction mixtures treated or untreated with trehalase was dried, dissolved in pyridine, and trimethyl-silylated. The resulting products were analyzed on gas chromatography (hereinafter abbreviated as "GLC") under the conditions of using a stainless steel column, 3 mm in diameter and 2 m in length, packed with 2% "SILICONE OV-17/CHROMOSOLB W", a resin for GLC commercialized by GL Sciences Inc., Tokyo, Japan, nitrogen gas as a carrier gas, flow rate of 40 ml/min, column oven temperatures of 160°–320° C., and heating-up rate of 7.5° C./min. Saccharide components were detected by a hydrogen flame ionization detector.

As a result, it was revealed that the retention time of a peak for a glucosyl-transferred saccharide, formed from D-glucose and β-D-glucose-1-phosphoric acid by the action of the present trehalose phosphorylase, was agreed with that of authentic trehalose, and that the trehalase treatment diminished the peak and formed D-glucose. Considering the substrate specificity of trehalase, it was speculated that the glucosyl-transferred saccharide was trehalose.

Experiment 8

Glucosyl-D-galactoside

To identify the glucosyl-transferred saccharide formed via the saccharide-transferring reaction to D-galactose by the present trehalose phosphorylase, the glucosyl-transferred saccharide was prepared, isolated, and examined for structure. The procedures were as follows: Provide an aqueous solution containing 5% trehalose, 2.5% D-galactose, and 5 mM sodium dihydrogenphosphate, adjust the aqueous solution to give a pH of 5.0, add to the solution 15 units/g β-D-glucose-1-phosphoric acid of a purified trehalose phosphorylase obtained by the method in Experiment 2, enzymatically react the solution at 60° C. for 72 hours, heat the reaction mixture at 100° C. for 10 min to inactivate the remaining enzyme, and analyze on GLC a sample from the resulting mixture according to the method in Experiment 7. As a result, it was confirmed that the reaction mixture contained a relatively-large amount of a substance with a retention time differing from those of trehalose, D-galactose, D-glucose, and β-D-glucose-1-phosphoric acid, estimating that it was the glucosyl-transferred saccharide. Based on the data from GLC, the yield of the saccharide was about 30%. The remaining reaction mixture was adjusted to give a pH of 7.0, admixed with 25 units/g trehalose remained, and enzymatically reacted at 45° C. for 20 hours to decompose trehalose remaining in the reaction mixture. The resultant was heated at 100° C. for 10 min to inactivate the remaining trehalase, decolored with activated charcoals, filtered, desalted and purified using ion exchange resins in H- and OH-form, concentrated up to give a concentration of about 50%, and subjected to the column chromatography below, followed by collecting fractions rich in the glucosyl-transferred saccharide.

The resin used for fractionation was "XT-1016", an alkali metal strong-acid cation exchange resin, Na-form, polymerization degree of 4%, commercialized by Tokyo Organic Chemical Industries, Ltd., Tokyo, Japan, and the resin was suspended in water, packed in four jacketed-stainless steel columns, 3 cm in diameter and one meter in length each, which were cascaded in series to give a total gel-bed depth of about 4 m. Keeping the inner column temperature at 40° C., a saccharide solution was fed to the columns in a volume of 5 v/v % to the resin, followed by feeding to the columns water heated to 40° C. at a flow rate of SV (space velocity) 0.15 to fractionate the saccharide solution and collecting fractions rich in the glucosyl-transferred saccharide.

The fractions were pooled, desalted, purified, and concentrated into an about 40% concentrate which was then chromatographed on a column packed with "YMC-Pack ODS", an octadecyl silica gel commercialized by YMC Co., Ltd., Kyoto, Japan, to collect fractions containing the glucosyl-transferred saccharide. The fractions were pooled and concentrated into an about 40% concentrate which was then re-applied to the above column chromatography. The resulting solution rich in the glucosyl-transferred saccharide was desalted, purified, concentrated, and dried in vacuo to obtain a powdery product containing the saccharide in a yield of about 20%, d.s.b., to the material saccharide used in the enzymatic reaction. In accordance with the method in Experiment 7, the powdery product was analyzed on GLC, revealing that it contained about 98% of the glucosyl-transferred saccharide, d.s.b.

The powdery product rich in the glucosyl-transferred saccharide was subjected to GLC analysis after decomposed with acids, revealing that the saccharide produced D-glucose and D-galactose in a molar ratio of about 1:1 when decomposed with acids. The powdery product was methylated, hydrolyzed by acids, reduced, and acetylated to obtain partial methylhexytolacetate which was then analyzed on GLC to detect 2,3,4,6-tetra-O-methyl-1,5-di-O-acetylglucitol, and 2,3,4,6-tetra-O-methyl-1,5-di-O-acetylgalactitol. The data indicates that the glucosyl-transferred saccharide is composed of D-glucose and D-galactose in a molar ratio of 1:1 where both the OH-group at C-1 of D-glucose and the OH-group at C-1 of D-galactose relate to the bonding between these saccharides.

To examine the structure of the glucosylgalactoside in more detail, the saccharide was measured for specific rotation and $^{13}$C-NMR spectrum. As a result, it gave $[\alpha]^D_{20}$=+223° (c=0.97, H$_2$O) and $^{13}$C-NMR spectra (100 MHz, D$_2$O):σppm from TSP of 96.16, 95.97, 75.37, 74.94, 74.14, 73.90, 72.53, 72.11, 71.80, 70.76, 64.03, and 63.37. These data were nearly agreed with the authentic data of a chemically synthesized compound, α-D-galactopyranosyl α-D-glucopyranoside, and this confirmed that the glucosylgalactoside was glucosyl-D-galactoside, i.e., α-D-galactopyranosyl α-D-glucopyranoside, a disaccharide composed of D-glucose and D-galactose bound in an α-1,1 linkage.

Experiment 9

Acute Toxicity Test

Acute toxicity tests of a powdery product rich in glucosyl-D-galactoside obtained by the method in Experiment 8, a powdery product rich in glucosyl-D-xyloside obtained by the method in Example A-12, a powdery product rich in glucosyl-D-fucoside obtained by the method in Example A-14, and a powder-product rich in glucosyl-L-fucoside obtained by the method in Example A-15 were respectively tested in 7-week-old dd-strain mice by administering orally. As a result, no mouse died even when administered with their maximum doses, i.e., 50 g/kg mouse by weight. The data indicates that these saccharides are extremely low in toxicity.

Example A explains the present trehalose phosphorylase, DNA encoding the enzyme, and process for producing saccharides containing glucosyl-transferred saccharides prepared by using the enzyme, and of course, these embodiments do not limit the present invention:

EXAMPLE A-1

Enzyme Solution

*Thermoanaerobium brockii*, ATCC 35047, was cultured for about 30 hours in a fresh preparation of the same medium as used in Experiment 1, except for setting the temperature to 65° C., using a fermenter under anaerobic conditions according to the method in Experiment 1. The resulting culture was centrifuged to obtain cells which were then disrupted by ultrasonic and centrifuged. The supernatant was fed to a column packed with "DEAE-TOYOPEARL® GEL" to be adsorbed thereupon, and eluted from the column by feeding an aqueous linear gradient of sodium chloride increasing from 0M to 0.5M, followed by collecting fractions with a trehalose phosphorylase activity eluted at about 0.1M sodium chloride. The fractions were pooled and concentrated with an ultrafiltration membrane to obtain an enzyme solution with about 20 units/ml of trehalose phosphorylase in a yield of about 40% to the total activity of the material culture.

EXAMPLE A-2

Preparation of DNA

According to the method in Experiment 1, a seed of *Thermoanaerobium brockii*, ATCC 35047, was inoculated into 11 L of a fresh preparation of the same nutrient culture medium as used in Experiment 1, and cultured at 60° C. for 24 hours. The proliferated cells were separated from the culture by centrifugation, suspended in an adequate amount of Tris-EDTA-saline buffer (hereinafter abbreviated as "TES buffer") (pH 8.0), admixed with 0.05 w/v % of lysozyme to the cell suspension, and incubated at 37° C. for 30 min. Thereafter, the enzyme-treated mixture was freezed at -80° C. for one hour, and admixed successively with TES buffer (pH 9.0) and a mixture solution of TES buffer-phenol heated to 60° C., followed by sufficiently stirring and cooling the mixture, centrifuging the resultant, and collecting the formed upper-layer. Twofold volumes of cooled ethanol was added to the layer, and the formed sediment was collected, dissolved in an adequate amount of SSC buffer (pH 7.1), admixed with 7.5 μg ribonuclease and 125 μg protease, and incubated at 37° C. for one hour. To the resulting mixture was added a mixture solution of chloroform and isoamyl alcohol, followed by stirring and allowing to stand the mixture, and collecting the formed upper-layer. After adding cooled ethanol to the layer, the formed sediment was collected, rinsed with 70 v/v % cooled ethanol, and dried in vacuo to obtain a DNA. The DNA was dissolved in SSC buffer (pH 7.1) to give a concentration of about one mg/ml, and freezed at -80° C.

EXAMPLE A-3

Preparation of Transformant and Recombinant DNA

One ml of the DNA solution in Example A-2 was placed in a container, admixed with about 20 units of a restriction enzyme, Alu I, and incubated at 37° C. for 30 min to partially digest the DNA. The resulting mixture was subjected to sucrose density ultrafiltration to collect a DNA fragment of about 2,000–5,000 base pairs. In parallel, "Bluescript® II SK(+)", a plasmid vector commercialized by Stratagene Cloning Systems, California, USA, was completely cleaved with a restriction enzyme, Sma I, and 0.3 μg of the cleaved vector and about 3 μg of the DNA fragment were ligated using "DNA LIGATION KIT", Takara Shuzo Co., Ltd., Otsu, Shiga, Japan, according to the procedure attached to the kit. Using the recombinant DNA thus obtained, 100 μg of "EPICURIAN COLI® XL1-BLUE", a microorganism of the species *Escherichia coli* commercialized by Stratagene Cloning Systems, California, USA, was transformed by conventional competent cell method to obtain a gene library.

The resulting transformants as a gene library were inoculated into agar plate (pH 7.0), prepared in a usual manner, containing 10 g/l trypton, 5 g/l yeast extract, 5 g/l sodium chloride, 75 mg/l sodium salt of ampicillin, and 50 mg/l 5-bromo-4-chloro-3-indolyl-β-galactoside, and cultured at 37° C. for 18 hours, followed by fixing about 5,000 white colonies, formed on the plate, onto "HYBOND-N+", a nylon film commercialized by Amersham Corp., Div. Amersham International, Arlington, Heights, USA. Based on the amino acids 9–15 in the N-terminal region of SEQ ID NO:6 revealed in Experiment 4, an oligonucleotide with a nucleotide sequence, represented by 5'-TAYCCNTTYGARGAYTGGGT-3' (SEQ ID NO:9), was chemically synthesized, and labelled with [γ-$^{32}$P]ATP and T4 polynucleotide kinase to obtain a synthesized DNA as a first probe. Among the colonies fixed on the nylon film, three colonies strongly hybridized with the first probe was selected by applying conventional colony-hybridization method. These three colonies were fixed on a nylon film similarly as above. Based on the amino acids 1–7 of SEQ ID NO:7 revealed in Experiment 4, an oligonucleotide with a nucleotide sequence, represented by 5'-AAYTAYGAYTAYTAYGARCC-3' (SEQ ID NO:10), was chemically synthesized, and labelled with [γ-$^{32}$P]ATP and T4 polynucleotide kinase to obtain a synthesized DNA as a second probe. Among the above three colonies fixed on the nylon film, one colony strongly hybridized with the second probe was selected by applying conventional colony-hybridization method and named "TTP4" as a transformant.

The transformant TTP4 was in a conventional manner inoculated into L-broth (pH 7.0) containing 100 μg/ml of sodium salt of ampicillin, and incubated at 37° C. for 24 hours under rotary-shaking conditions. After completion of the culture, the culture was centrifuged to obtain cells which were then treated with conventional alkali-SDS method to extract a recombinant DNA. Conventional dideoxy analysis of the recombinant DNA revealed that it contained a DNA with the nucleotide sequence of SEQ ID NO:8 consisting of 3,345 base pairs derived from *Thermoanaerobium brockii*, ATCC 35047. As shown in SEQ ID NO:8, it was revealed that a nucleotide sequence, consisting of the bases 596–2, 917 in SEQ ID NO:8, encodes an amino acid sequence consisting of 774 amino acids. Comparing the amino acid sequence deduced from the nucleotide sequence and the N-terminal and internal amino acid sequences of the present trehalose phosphorylase confirmed in Experiment 4, i.e., SEQ ID NOs:1–3 and SEQ ID NOs:6–7, SEQ ID NOs:1–3 were respectively agreed with the amino acids 2–6, 308–312, and 633–637 in SEQ ID NO:8, while SEQ ID NOs:6–7 were respectively agreed with the amino acids 2–31 and 633–647 in SEQ ID NO:8.

Figure 5:
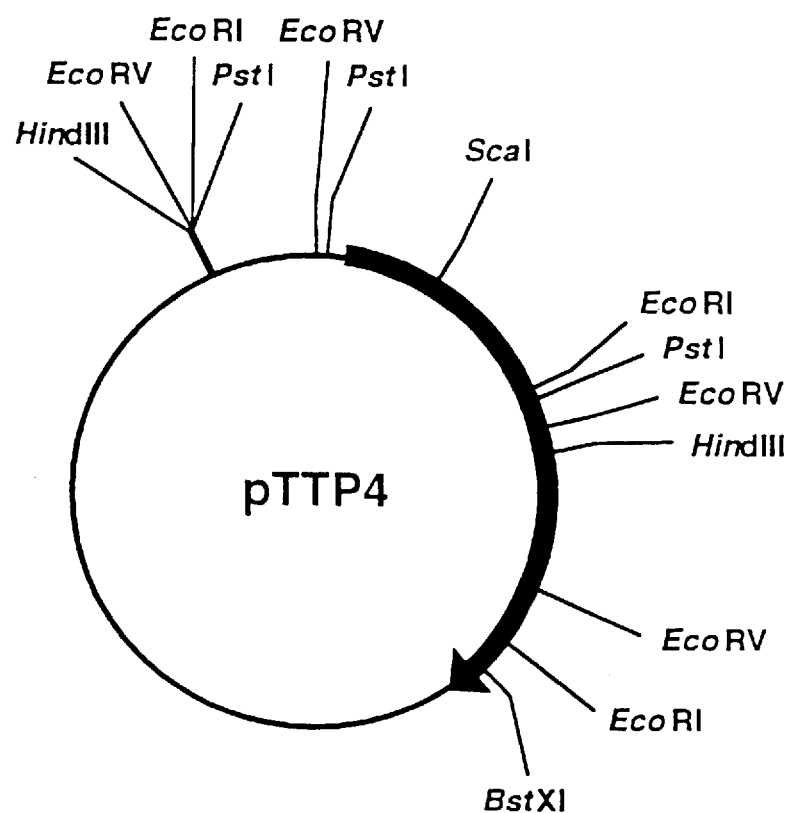
FIG. 5 is a restriction map of the present recombinant DNA. In the figure, an arrow shows a DNA encoding the present trehalose phosphorylase.

These data indicate that the present trehalose phosphorylase has the amino acid sequence of SEQ ID NO:4, and the enzyme of *Thermoanaerobium brockii*, ATCC 35047, is encoded by a DNA having the nucleotide sequence of SEQ ID NO:5. The recombinant DNA, which was obtained by the above methods and revealed its nucleotide sequence, was named "pTTP4". As shown in FIG. 5, the recombinant DNA is positioned at the down stream of the recognition site by a restriction enzyme, Pst I.

EXAMPLE A-4

Production of Trehalose Phosphorylase by Transformant

One hundred ml of an aqueous solution, containing 16 g/l polypeptone, 10 g/l yeast extract, and 5 g/l sodium chloride, was placed in a 500-ml Erlenmeyer flask, autoclaved at 121° C. for 15 min, cooled, aseptically adjusted to pH 7.0, and aseptically admixed with 10 mg sodium salt of ampicillin into a liquid nutrient medium. The transformant TTP4 in Example A-3 was inoculated into the medium, and incubated at 37° C. for about 20 hours under aeration-agitation conditions to obtain a seed culture. According to the preparation of the seed culture, 7 L of a fresh preparation of the same nutrient culture medium as used in the seed culture was placed in a 10-l fermenter, inoculated with 70 ml of the seed culture, and subjected to an incubation for about 20 hours under aeration-agitation conditions. The resulting culture was in a conventional manner centrifuged to collect cells which were then suspended in 10 mM phosphate buffer (pH 7.0), ultrasonicated for cell disruption, and centrifuged to remove insoluble substances, followed by collecting a supernatant. The supernatant was dialyzed against 10 mM phosphate buffer, and assayed for trehalose phosphorylase activity in the supernatant, revealing that about 700 units/l culture of the enzyme was produced.

As a first control, a seed of *Escherichia coli* XL1-Blue strain was inoculated into a nutrient culture medium similarly as in the culture of the above transformant except that the ampicillin was not added to the culture medium, and cultured. The proliferated cells were disrupted, followed by collecting and dialyzing the supernatant. As a second control, according to the method in Experiment 1, a seed of *Thermoanaerobium brockii*, ATCC 35047, was stationary cultured at 60° C. in a nutrient culture medium consisting of the same ingredients as used in the culture for the transformant except that the ampicillin was not used, and similarly as in the case of the transformant, the cells in the culture were disrupted, followed by collecting and dialyzing the supernatant. No enzyme activity of the present enzyme was detected in the dialyzed solution as the first control. The dialyzed solution as the second control had an enzyme activity of about 2 units/l culture which was lower than that of the transformant TTP4.

In accordance with the method in Experiment 2, the dialyzed solution in Example A-4 was purified on column chromatographies using "DEAE-TOYOPEARL® 650 GEL" and "ULTROGEL® AcA44 RESIN", and the purified enzyme was analyzed in accordance with the method in Experiment 3, revealing that it had a molecular weight of 88,000±5,000 daltons on SDS-PAGE, molecular weight of 190,000±10,000 daltons on gel filtration chromatography, isoelectric point of 5.4±0.5 on electrofocusing using polyacrylamide gel, optimum temperature of about 70° C., optimum pH of about 7.0–7.5, thermal stability of up to 60° C., and pH stability of about 6.0–9.0, all of which were substantially the same as those of the enzyme prepared in Experiments 1 and 2. These results indicate that the present trehalose phosphorylase can be sufficiently produced by recombinant DNA technology, and the enzyme yield can be significantly increased thereby.

EXAMPLE A-5

Enzyme Solution

The transformant TTP4 in Example A-3 was cultured in a nutrient culture medium by the method in Example A-4. Cells obtained by centrifuging the culture were disrupted by ultrasonics, and a supernatant of the disrupted cell suspension was measured for trehalose phosphorylase activity. The activity was about 0.7 unit/ml culture. The supernatant was concentrated with an ultrafiltration membrane, and the concentrate was dialyzed to obtain an enzyme solution with an activity of about 10 units/ml of trehalose phosphorylase in a yield of about 70% to the total enzyme activity of the culture.

EXAMPLE A-6

Saccharide Solution Containing Trehalose

To 25 mM of dipotassium hydrogenphosphate-citric acid buffer (pH 6.0) containing 5% maltose were added 5 units/g maltose of a commercially available bacterial maltose phosphorylase, and 50 units/g maltose of trehalose phosphorylase obtained by the method in Example A-1, followed by the incubation at 30° C. for 120 hours. The reaction mixture was heated at 100° C. for 30 min to inactivate the remaining enzymes, cooled, decolored with activated charcoals in a conventional manner, filtered, desalted and purified with ion exchange resins in H- and OH-form, and further concentrated to obtain a 75% syrupy saccharide solution containing trehalose in a yield of about 95% to the material, d.s.b.

The product, which contains about 45% trehalose, d.s.b., and has a satisfactory sweetness and an adequate viscosity and humectancy, can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-7

Trehalose Enriched Powder

A saccharide solution, as a material, containing about 45% trehalose, d.s.b., obtained by the reaction and purification in Example A-6, was adjusted to give a concentration of about 20%, d.s.b., which was then mixed with 5 units/g dry solid of glucoamylase and incubated at pH 4.5 and 40° C. for 16 hours to decompose the remaining maltose. The reaction mixture was heated at 100° C. for 30 min to suspend the enzymatic reaction, then concentrated into an about 40% solution. To increase the trehalose content, the concentrated solution was fractionated by providing four jacketed-stainless steel columns, 3 cm in diameter and one meter in length each, packed with a water suspension of "XT-1016", an alkali metal strong-acid cation exchange resin, Na-form, polymerization degree of 4%, commercialized by Tokyo Organic Chemical Industries, Ltd., Tokyo, Japan, which were cascaded in series to give a total gel-bed depth of about 4 m, feeding 5 v/v % of the solution to the resin, fractionating the solution by feeding water heated to 40° C. to the columns at SV 0.15, and collecting the resulting trehalose rich fractions. The fractions were pooled, concentrated, dried in vacuo, and pulverized to obtain a trehalose rich powder in a yield of about 40% to the material, d.s.b.

The product contains about 95% trehalose, d.s.b., and has a satisfactorily tastable sweetness and adequate humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-8

Saccharide Solution Containing Glucosyl-D-galactoside

An aqueous solution containing 5% trehalose, 5% D-galactose, and 5 mM sodium dihydrogenphosphate was adjusted to give a pH of 5.0, admixed with 10 units/g trehalose of a trehalose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain an about 75% syrupy saccharide solution containing glucosylsorbose in a yield of about 95% to the material, d.s.b.

The product contains about 22% glucosyl-D-galactoside, d.s.b., and has a high-quality sweetness and adequate viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-9

Saccharide Solution Containing Glucosyl-D-galactoside

An aqueous solution, containing 10% trehalose, 5% D-galactose, and 5 mM sodium dihydrogenphosphate, was adjusted to give a pH of 6.0, admixed with 30 units/g trehalose of a trehalose phosphorylase obtained by the method in Example A-1, and enzymatically reacted at 60° C. for 96 hours. The reaction mixture was heated at 90° C. for 30 min to inactivate the remaining enzyme and cooled. Thereafter, 5% by wet weight of commercially available baker's yeasts was added to the resulting mixture to assimilate D-glucose in the reaction mixture while controlling the pH at 5–6 by the addition of 1-N sodium chloride solution and keeping the reaction temperature at 27° C. for 6 hours. The reaction mixture was centrifuged to remove the yeasts, and the resulting supernatant was in a conventioral manner decolored with activated charcoals, filtered, desalted and purified with ion exchangers in H- and OH-form, and concentrated to obtain a 75% syrup, d.s.b., in a yield of about 65% to the material, d.s.b.

The product contains about 40% glucosyl-D-galactoside, d.s.b., and has a high-quality sweetness and adequate viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-10

Glucosyl-D-galactoside Rich Powder

A saccharide solution, as a material, containing about 22% glucosyl-D-galactoside, d.s.b., obtained by the reaction and purification of Example A-8, was adjusted to give a concentration of about 45%, d.s.b. To increase the content of glucosyl-D-galactoside, the resulting solution was fractionated by providing four jacketed-stainless steel columns, 3 cm in diameter and one meter in length each, which were packed with a water suspension of "XT-1016", an alkali metal strong-acid cation exchange resin, Na-form, polymerization degree of 4%, commercialized by Tokyo Organic Chemical Industries, Ltd., Tokyo, Japan, and cascaded in series to give a total gel-bed depth of about 4 m, feeding 5 v/v % of the solution to the resin, fractionating the solution by feeding water heated to 40° C. to the columns at SV 0.15 while keeping the inner column temperature of 40° C., and collecting the resulting glucosyl-D-galactoside rich fractions. The fractions were pooled, concentrated, dried in vacuo, and pulverized to obtain a glucosyl-D-galactoside rich powder in a yield of about 25% to the material, d.s.b.

The product contains about 70% glucosyl-D-galactoside, d.s.b., and has a high-quality sweetness and adequate viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-11

Saccharide Solution Containing Glucosyl-D-xyloside

An aqueous solution containing 5% trehalose, 2.5% D-xylose, and 5 mM sodium dihydrogenphosphate was adjusted to a pH of 5.0, admixed with 15 units/g trehalose of a trehalose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoal in a conventional manner, filtered, desalted and purified with ion exchange resins in H- and OH-form, and further concentrated to obtain an about 75% syrup in a yield of about 95% to the material, d.s.b.

The product contains about 20% glucosyl-D-xyloside, d.s.b., and has a high-quality sweetness and adequate viscosity and humectancy, and it can be arbitrarily used in food products, cosmetics, pharmaceuticals, and shaped bodies.

EXAMPLE A-12

Glucosyl-D-xyloside Rich Powder

A saccharide solution as a material containing about 20% glucosyl-D-xyloside, d.s.b., obtained by the reaction and purification in Example A-11, was adjusted to give a concentration of about 45%, d.s.b. To increase the content of glucosyl-D-xyloside, the resulting solution was column chromatographed according to the method in Example A-10 except for using "DOWEX 50WX4 (Ca-form)", an alkaline-earth metal strong-acid cation exchange resin commercialized by The Dow Chemical Co., Midland, Mich., USA, to collect glucosyl-D-xyloside rich fractions. The fractions were pooled, purified, concentrated, dried in vacuo, and pulverized to obtain a glucosyl-D-xyloside rich powder in a yield of about 25%, d.s.b.

The product contains about 60% glucosyl-D-xyloside, d.s.b., and has a high-quality sweetness and adequate viscosity and humectancy, and it can be arbitrarily used in food products, cosmetics, pharmaceuticals, and shaped bodies.

EXAMPLE A-13

Saccharide Solution Containing Glucosyl-D-fucoside

An aqueous solution, containing 5% trehalose, 2.5% D-fucose, and 5 mM disodium hydrogenphosphate, was adjusted to give a pH of 5.0, admixed with 20 units/g trehalose of a trehalose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain an about 75% syrup in a yield of about 95% to the material, d.s.b.

The product contains about 20% glucosyl-D-fucoside, d.s.b., and has a high-quality sweetness and adequate viscosity and humectancy, and it can be arbitrarily used in food products, cosmetics, pharmaceuticals, and shaped bodies.

EXAMPLE A-14

Saccharide Powder Rich in Glucosyl-D-fucoside

An aqueous solution, containing about 5% trehalose, 2.5% D-fucose, and 5 mM sodium dihydrogenphosphate, was adjusted to give a pH of 5.0, admixed with 20 units/g trehalose of a trehalose phosphorylase obtained by the method in Example A-1, and enzymatically reacted at 60° C. for 72 hours. The reaction mixture was heated at 100° C. while keeping the pH to alkaline pHs of over 10, cooled, decolored with activated charcoals in a conventional manner, filtered, desalted and purified with ion exchange resins in H- and OH-form, and further concentrated to obtain a powder containing glucosyl-D-fucoside in a yield of about 60% to the material, d.s.b.

The product contains about 50% glucosyl-D-fucoside, d.s.b., and has a high-quality sweetness and adequate viscosity and humectancy, and it can be arbitrarily used in food products, cosmetics, pharmaceuticals, and shaped bodies.

EXAMPLE A-15

Saccharide Powder Containing Glucosyl-L-fucoside

An aqueous solution, containing about 5% trehalose, 2.5% L-fucose, and 5 mM sodium dihydrogenphosphate, was adjusted to give a pH of 6.0, admixed with 15 units/g trehalose of a trehalose phosphorylase obtained by the method in Example A-1, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain a powder containing glucosyl-L-fucoside in a yield of about 95% to the material, d.s.b.

The product contains about 20% glucosyl-L-fucoside, d.s.b., and has a high-quality sweetness and adequate humectancy, and it can be arbitrarily used in food products, cosmetics, pharmaceuticals, and shaped bodies.

EXAMPLE A-16

Saccharide Solution Containing Trehalose

To 25 mM dipotassium hydrogenphosphate-citric acid buffer (pH 6.0) containing 5% maltose were added 5 units/g maltose of a commercially available maltose phosphorylase and 50 units/g maltose of a trehalose phosphorylase preparation obtained by the method in Example A-5, and subjected to an enzymatic reaction at 30° C. for 120 hours. The reaction mixture was heated at 100° C. for 30 min to inactivate the remaining enzymes, cooled, decolored with activated charcoals in a conventional manner, filtered, desalted and purified with ion exchange resins in H- and OH-form, and further concentrated to obtain an about 75% syrup, d.s.b., in a yield of about 95% to the material, d.s.b.

The product contains about 45% trehalose, d.s.b., and has a high-quality sweetness and adequate viscosity and humectancy, and it can be arbitrarily used in food products, cosmetics, pharmaceuticals, and shaped bodies as a sweetener, taste-improving agent, stabilizer, growth-promoting agent for bifid bacteria, and mineral-absorption-promoting agent.

EXAMPLE A-17

Saccharide Solution Containing Glucosyl-D-fucoside

An aqueous solution, containing 5% trehalose, 2.5% D-fucose, and 5 mM disodium hydrogenphosphate, was adjusted to give a pH of 5.0, admixed with 20 units/g trehalose of a trehalose phosphorylase obtained by the method in Example A-5, and enzymatically reacted at 60° C. for 72 hours. The reaction mixture was heated at 90° C. for 30 min to inactivate the remaining enzyme, cooled, decolored with activated charcoals in a conventional manner, filtered, desalted and purified with ion exchange resins in H- and OH-form, and further concentrated to obtain an about 75% syrup in a yield of about 95% to the material, d.s.b.

The product contains about 20% glucosyl-D-fucoside, d.s.b., and has a high-quality sweetness and adequate viscosity and humectancy, and it can be arbitrarily used in food products, cosmetics, pharmaceuticals, and shaped bodies.

The following Example B explains the present saccharide compositions containing glucosyl-transferred saccharides:

EXAMPLE B-1

Sweetener

To one part by weight of a glucosyl-D-galactoside rich powder, obtained by the method in Example A-10, was added 0.05 part by weight of "αG SWEET", an α-glycosyl stevioside commercialized by Toyo Sugar Refining Co., Ltd., Tokyo, Japan, and the mixture was mixed to homogeneity into a powdery sweetener. The product is a high-quality sweetener with an about twofold-higher sweetening power of sucrose and a half calorific value of sucrose with respect to the sweetening powder. Therefore, the product can be satisfactorily used as a low-calorie sweetener to sweeten low-calorie food products for persons, who are restricted to take less calories, such as fat persons and diabetics. Since the product less produces insoluble glucans and acids by dental caries-inducing microorganisms, it can be suitably used to sweeten dental-caries inhibitory food products.

EXAMPLE B-2

Hard Candy

Thirty parts by weight of a saccharide solution containing glucosyl-D-galactoside, obtained by the method in Example A-9, was added to and dissolved by mixing in 80 parts by weight of hydrogenated malt syrup with a moisture content of 25%, and the resulting solution was concentrated up to give a moisture content of below 2% under reduced pressures, kneaded with one part by weight of citric acid and adequate amounts of a lemon flavor and coloring agent, followed by kneading and shaping the mixture into a hard candy. The product has a high-quality sweetness, lower humectancy, and satisfactory biting property without causing melting.

EXAMPLE B-3

Chewing Gum

Four parts by weight of a powder rich in glucosyl-D-xyloside, obtained by the method in Example A-12, was admixed with 3 parts by weight of glucose and 2 parts by weight of a gum base which had been melted by heating until softened, and further mixed with an adequate amount of a mint flavor, followed by shaping the mixture by kneading with a roll into a chewing gum. The product has a satisfactory texture and flavor.

EXAMPLE B-4

Chocolate

Fifteen parts by weight of a powder rich in glucosyl-D-fucoside, obtained by the method in Example A-14, was mixed with 40 parts by weight of cacao paste, 10 parts by weight of cacao butter, 10 parts by weight of sucrose, and 15 parts by weight of skim milk, and the mixture was passed through a refiner to lower the granular size. Thereafter, the resulting mixture was placed in a conche, mixed with 0.5 part by weight of lecithin, and kneaded up at 50° C. for two days and nights. The kneaded mixture was poured into a molding machine, shaped, and solidified into a chocolate. The product free of fat- and sugar-blooms has a satisfactory taste, flavor, and meltability on your tongue.

EXAMPLE B-5

Custard Cream

To 400 parts by weight of a powder rich in glucosyl-L-fucoside, obtained by the method in Example A-15, were added 500 parts by weight of corn starch, 500 parts by weight of maltose, and 5 parts by weight of salt, and the mixture was sufficiently mixed by passing through a sieve, mixed with 1,400 parts by weight of fresh eggs, stirred, gradually admixed with 5,000 parts by weight of a boiling milk, and heated over a slow fire while stirring. The heating was suspended when the corn starch completely gelatinized to show semitransparency, then cooled, mixed with a small amount of a vanilla flavor to obtain a custard cream. The product has a smooth surface and satisfactory taste free of strong sweetness.

EXAMPLE B-6

Uiro (starch paste)

To 90 parts by weight of a saccharide solution containing glucosyl-D-fucoside, obtained by the method in Example A-13, were added 90 parts by weight of rice powder, 20 parts by weight of corn starch, 20 parts by weight of sugar, one part by weight of matcha (a green tee) powder, and an adequate amount of water, and the mixture was kneaded, placed in a container, and steamed for 60 min into a matcha uiro. The product has a satisfactory gloss, biting property, flavor, and taste. The retrogradation of starch is well prevented, resulting in a relatively-long shelf life.

EXAMPLE B-7

Bettara-zuke (fresh radish pickles)

A premix for bettara-zuke was prepared by mixing to homogeneity one part by weight of a saccharide solution containing glucosyl-D-galactoside, obtained by the method in Example A-8, with 3 parts by weight of maltose, 0.05 part by weight of a licorice preparation, 0.008 part by weight of malic acid, 0.07 part by weight of sodium glutamate, 0.03 part by weight of potassium sorbate, and 0.2 part by weight of pullulan. Thirty kilograms of radish was first pickled with salt in a conventional manner, then pickled with sugar, and soaked in a seasoning solution, prepared with 4 kg of the premix, into the desired product. The product has a satisfactory color, gloss, and fragrance, as well as an adequate sweetness, and satisfactory biting property.

EXAMPLE B-8

Beverage with Lactic Acid Bacteria

One hundred and thirty parts by weight of a saccharide solution containing glucosyl-D-xyloside, obtained by the method in Example A-11, 175 parts by weight of skim milk, and 50 parts by weight of "NYUKAOLIGO®", a high lactosucrose content powder commercialized by Hayashibara Shoji, Inc., Okayama, Japan, were dissolved in 1,150 parts by weight of water, and the solution was sterilized at 65° C. for 30 min, cooled to 40° C., and in a conventional manner inoculated with 30 parts by weight of lactic acid bacteria as a starter, followed by the incubation at 37° C. for 8 hours to obtain the desired product. The product is a beverage containing lactic acid bacteria and having a satisfactory flavor and taste. The product contains oligosaccharides which stabilize the bacteria and promote the growth.

EXAMPLE B-9

Skin Cream

To 4 parts by weight of a powder rich in trehalose, obtained by the method in Example A-7, were added 2 parts by weight of polyoxyethylene glycol monostearate, 5 parts by weight of self-emulsifying glycerine monostearate, 2 parts by weight of α-glycosyl rutin, one part by weight of liquid paraffin, 10 parts by weight of glycerol trioctanate, and an appropriate amount of an antiseptic, and the mixture was dissolved by heating in a conventional manner, mixed with 5 parts by weight of 1,3-butylene glycol, and 66 parts by weight of refined water, emulsified with a homogenizer, and mixed with an appropriate amount of a flavor into a skin cream. The product with a well-spreadability can be arbitrarily used as a sunscreen, skin-refining agent, and skin-whitening agent.

EXAMPLE B-10

Toothpaste

Forty-five parts by weight of calcium hydrogen phosphate, 1.5 parts by weight of sodium lauryl sulfate, 25 parts by weight of glycerine, 0.5 part by weight of polyoxyethylene sorbitan laurate, 0.02 part by weight of saccharin, 0.05 part by weight of an antiseptic, and 13 parts by weight of water were mixed with 15 parts by weight of a saccharide solution rich in trehalose, obtained by the method in Example A-6, into a toothpaste.

The product, having a superior gloss and detergency, can be suitably used as a dentifrice.

EXAMPLE B-11

Nutrition for Intubation Feeding

A composition consisting of the following ingredients was prepared: 80 parts by weight of a powder rich in glucosyl-D-galactoside obtained by the method in Experiment 8, 190 parts by weight of dried egg yolk, 209 parts by weight of skim milk, 4.4 parts by weight of sodium chloride, 1.85 parts by weight of potassium chloride, 4 parts by weight of magnesium sulfate, 0.01 part by weight of thiamine, and 0.1 part by weight of sodium ascorbate, 0.6 part by weight of vitamin E acetate, and 0.04 part by weight of nicotine amide. Twenty-five grams aliquots of the composition were injected into small laminated aluminum bags which were then heat-sealed to obtain the desired product.

One bag of the product is dissolved in about 150–300 ml water into a supplemental nutrition feeding before administering to the nasal cavity, throat, or stomach.

EXAMPLE B-12

Strawberry Jam

One hundred and fifty parts by weight of fresh strawberries, 60 parts by weight of sucrose, 20 parts by weight of maltose, 40 parts by weight of a saccharide solution containing trehalose obtained by the method in Example A-16, 5 parts by weight of pectin, and one part by weight of citric acid. The mixture was boiled up in a pan and bottled into the desired product. The product has a satisfactory taste, flavor, and color.

EXAMPLE B-13

Sweetened Condensed Milk

In 100 parts by weight of fresh milk were dissolved one part by weight of sucrose and 3 parts by weight of a saccharide solution containing glucosyl-D-fucoside obtained by the method in Example A-17, and the solution was sterilized by heating on a plate heater, condensed to give a concentration of about 70%, and aseptically canned into the desired product. The product has a mild sweetness, flavor, and taste, and it can be arbitrarily used as a seasoning for food for infants, fruits, coffees, cocoas, and teas.

[Effect of the Invention]

As evident from the above, the present invention was made based on a finding of a novel trehalose phosphorylase which has a higher optimum temperature and thermal stability than those of conventional trehalose phosphorylases. The trehalose phosphorylase according to the present invention has a relatively-wide range pH-stability in which the optimum pH lies. The trehalose phosphorylase can be produced by microorganisms capable of producing the enzyme in a satisfactorily-high yield. Thus, when the present trehalose phosphorylase is allowed to contact with β-D-glucose-1-phosphoric acid as a saccharide donor in the presence of other saccharides, glucosyl-transferred saccharides including glucosyl-D-galactoside, which are conventionally known but scarcely obtainable, can be produced on an industrial-scale and in a relatively-low cost.

The glucosyl-transferred saccharides and saccharide compositions containing the same can be used as sweeteners with a relatively-high quality sweetness, taste-improving agents, quality-improving agents, body-imparting agents, viscosity-controlling agents, moisture-controlling agents, gloss-imparting agents, and supplemental nutrition agents in food products, cosmetics, pharmaceuticals, and shaped bodies. Because of these outstanding characteristics of the present invention, it greatly contributes to food, cosmetic, and pharmaceutical fields, and to agriculture, fishery, breeding, and chemical industries.

What is claimed:

1. A process for producing a saccharide composition containing a D-glucosyl-transferred saccharide, which comprises a step of contacting a trehalose phosphorylase with β-D-glucose-1-phosphoric acid, its salt or a mixture thereof, and other saccharide to produce the D-glucosyl-transferred saccharide, wherein said trehalose phosphorylase is obtainable from a microorganism of the genus Thermoanaerobium and which hydrolyzes trehalose in the presence of an inorganic phosphoric acid, its salt or a mixture thereof to form D-glucose and said β-D-glucose-1-phosphoric acid, its salt or a mixture thereof.

2. The process of claim 1, wherein said β-D-glucose-1-phosphoric acid, its salt or a mixture thereof is one obtained by contacting the trehalose phosphorylase with trehalose in the presence of an inorganic phosphoric acid, its salt or a mixture thereof, contacting a maltose-phosphorylase with maltose in the presence of an inorganic phosphoric acid, its salt or a mixture thereof, or contacting a kojibiose-phosphorylase with kojibiose in the presence of an inorganic phosphoric acid, its salt or a mixture thereof.

3. The process of claim 1, wherein said other saccharide is one selected from the group consisting of D-xylose, D-galactose, D-glucose, D-fucose, and L-fucose.

4. The process of claim 1, which comprises a technique selected from the group consisting of column chromatographies and fermentation methods using yeasts as methods for removing impurities other than the glucosyl-transferred saccharides produced during the enzymatic reaction or remaining in the reaction mixture or both.

5. A process for producing trehalose, which comprises contacting a trehalose phosphorylase with maltose along with a maltose-phosphorylase in the presence of an inorganic phosphoric acid, its salt or a mixture thereof to produce trehalose, or contacting the trehalose phosphorylase with kojibiose along with a kojibiose-phosphorylase in the presence of an inorganic phosphoric acid, its salt or a mixture thereof to produce trehalose, wherein said trehalose phosphorylase is obtainable from a microorganism of the genus Thermoanaerobium and which hydrolyzes trehalose in the presence of an inorganic phosphoric acid, its salt or a mixture thereof to form D-glucose and $\beta$-D-glucose-1-phosphoric acid, its salt or a mixture thereof.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( v ) FRAGMENT TYPE:N-terminal fragment ( x i ) SEQUENCE DESCRIPTION:SEQ ID NO:1:

Ala  Asn  Lys  Thr  Lys
    1                            5

( 2 ) INFORMATION FOR SEQ ID NO:2:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( v ) FRAGMENT TYPE:internal fragment ( x i ) SEQUENCE DESCRIPTION:SEQ ID NO:2:

Glu  Gln  Glu  Glu  Phe
    1                            5

( 2 ) INFORMATION FOR SEQ ID NO:3:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:peptide ( v ) FRAGMENT TYPE:internal fragment ( x i ) SEQUENCE DESCRIPTION:SEQ ID NO:3:

Asn  Tyr  Asp  Tyr  Tyr
    1                            5

( 2 ) INFORMATION FOR SEQ ID NO:4:

( i ) SEQUENCE CHARACTERISTICS:
        ( A ) LENGTH:773 amino acids
        ( B ) TYPE:amino acid
        ( D ) TOPOLOGY:linear ( i i ) MOLECULE TYPE:peptide ( x i ) SEQUENCE DESCRIPTION:SEQ ID NO:4:

Ala  Asn  Lys  Thr  Lys  Lys  Pro  Ile  Tyr  Pro  Phe  Glu  Asp  Trp  Val  Ile
    1                  5                      10                      15

Arg  Glu  Thr  Gln  Phe  Ser  Ile  Asp  Thr  Asn  Tyr  Arg  Asn  Glu  Thr  Ile
                          20                      25                      30

Phe  Thr  Leu  Ala  Asn  Gly  Tyr  Ile  Gly  Met  Arg  Gly  Thr  Phe  Glu  Glu
                          35                      40                      45

Arg  Tyr  Ser  Gly  Pro  Lys  Asn  Thr  Ser  Phe  Asn  Gly  Thr  Tyr  Ile  Asn

|     |     |     |     |     | 50  |     |     |     |     | 55  |     |     |     |     | 60  |
| --- | --- | --- | --- | --- | --- | --- | --- | --- | --- | --- | --- | --- | --- | --- | --- |

Gly Phe Tyr Glu Ile His Asp Ile Val Tyr Pro Glu Gly Gly Tyr Gly
65                  70                  75                  80

Phe Ala Lys Ile Gly Gln Thr Met Leu Asn Val Ala Asp Ser Lys Ile
                85                  90                  95

Ile Lys Leu Tyr Val Asp Gly Glu Glu Phe Asp Leu Leu Gln Gly Lys
                100                 105                 110

Ile Leu Phe Tyr Glu Arg Val Leu Asp Met Lys Lys Gly Phe Val Glu
            115                 120                 125

Arg Lys Val Lys Trp Glu Ser Pro Thr Gly Lys Ile Leu Glu Val Lys
        130                 135                 140

Ile Lys Arg Ile Val Ser Leu Asn Arg Gln His Leu Ala Ala Ile Ser
145                 150                 155                 160

Phe Thr Met Gln Pro Val Asn Phe Thr Gly Lys Ile Arg Phe Val Ser
                165                 170                 175

Ala Ile Asp Gly Asn Val Ser Asn Ile Asn Asp Ser Glu Asp Val Arg
            180                 185                 190

Val Gly Ser Asn Leu Lys Gly Lys Val Leu Lys Thr Ile Asp Lys Ser
        195                 200                 205

Val Glu Gly Leu Lys Gly Trp Ile Val Gln Lys Thr Gln Lys Ser Asn
    210                 215                 220

Phe Ser Tyr Ala Cys Ala Ile Asp Asn Val Leu Val Ala Asp Ser Lys
225                 230                 235                 240

Tyr Glu Val Ser Asn Ser Leu Glu Glu Asp Gly Val Lys Val Ile Val
                245                 250                 255

Asp Leu Glu Ala Glu Lys Gly Thr Ser Tyr Thr Leu Asn Lys Phe Ile
            260                 265                 270

Ser Tyr Tyr Thr Ser Lys Asp Phe Asp Glu Asn Lys Leu Val Ala Leu
        275                 280                 285

Ala Leu Glu Glu Ile Glu Lys Ala Lys Asn Asp Gly Phe Glu Thr Ile
    290                 295                 300

Glu Lys Glu Gln Glu Glu Phe Leu Asn Ser Phe Trp Lys Asp Ala Asp
305                 310                 315                 320

Val Ile Ile Glu Gly Asp Lys Ala Leu Gln Gln Gly Ile Arg Phe Asn
                325                 330                 335

Glu Phe His Leu Leu Gln Ser Val Gly Arg Asp Gly Lys Thr Asn Ile
            340                 345                 350

Ala Ala Lys Gly Leu Thr Gly Gly Tyr Glu Gly His Tyr Phe Trp
        355                 360                 365

Asp Ser Asp Ile Tyr Ile Met Pro Phe Phe Leu Tyr Thr Lys Pro Glu
    370                 375                 380

Ile Ala Lys Ala Leu Val Met Tyr Arg Tyr Asn Leu Leu Asp Ala Ala
385                 390                 395                 400

Arg Ser Arg Ala Lys Glu Leu Gly His Lys Gly Ala Leu Tyr Pro Trp
                405                 410                 415

Arg Thr Ile Asp Gly Pro Glu Cys Ser Ala Tyr Phe Pro Ala Gly Thr
            420                 425                 430

Ala Gln Tyr His Ile Asn Ala Asp Ile Val Tyr Ala Leu Lys Arg Tyr
        435                 440                 445

Val Glu Ala Thr Asn Asp Val Asp Phe Leu Tyr Asp Tyr Gly Cys Glu
    450                 455                 460

Ile Leu Phe Glu Thr Ala Arg Phe Trp Glu Asp Leu Gly Ala Tyr Ile
465                 470                 475                 480

| | | | | | | | | | | | | | | |
|---|---|---|---|---|---|---|---|---|---|---|---|---|---|---|
| Pro | Leu | Lys | Gly | Asn 485 | Lys | Phe | Cys | Ile 490 | Asn | Cys | Val | Thr | Gly 495 | Pro | Asp |
| Glu | Tyr | Thr | Ala 500 | Leu | Val | Asp | Asn 505 | Asn | Ala | Tyr | Thr | Asn 510 | Tyr | Met | Ala |
| Lys | Met | Asn 515 | Leu | Glu | Tyr | Ala | Tyr 520 | Asp | Ile | Ala | Asn | Lys 525 | Met | Lys | Lys |
| Glu | Val 530 | Pro | Gln | Lys | Tyr | Gln 535 | Lys | Val | Ala | Ser | Lys 540 | Leu | Asn | Leu | Lys |
| Asp 545 | Glu | Glu | Ile | Val | Ala 550 | Trp | Lys | Lys | Ala | Ala 555 | Asp | Asn | Met | Tyr | Leu 560 |
| Pro | Tyr | Ser | Lys | Glu 565 | Leu | Asp | Ile | Ile | Pro 570 | Gln | Asp | Asp | Ser | Phe 575 | Leu |
| Tyr | Lys | Glu | Arg 580 | Ile | Thr | Val | Asp | Glu 585 | Ile | Pro | Glu | Asp | Gln 590 | Phe | Pro |
| Leu | Leu | Leu 595 | His | Trp | His | Tyr | Leu 600 | Asn | Ile | Tyr | Arg | Tyr 605 | Gln | Ile | Cys |
| Lys | Gln 610 | Pro | Asp | Val | Leu | Leu 615 | Leu | Met | Phe | Leu | Gln 620 | Arg | Glu | Lys | Phe |
| Thr 625 | Lys | Asp | Glu | Leu | Lys 630 | Lys | Asn | Tyr | Asp | Tyr 635 | Glu | Pro | Ile | Thr 640 |
| Thr | His | Asp | Ser | Ser 645 | Leu | Ser | Pro | Ala | Ile 650 | Phe | Ser | Ile | Leu | Ala 655 | Asn |
| Glu | Ile | Gly | Tyr 660 | Thr | Asp | Lys | Ala | Tyr 665 | Lys | Tyr | Phe | Met | Met 670 | Thr | Ala |
| Arg | Met | Asp 675 | Leu | Asp | Asp | Tyr | Asn 680 | Asp | Asn | Val | Lys | Asp 685 | Gly | Ile | His |
| Ala | Ala 690 | Ser | Met | Ala | Gly | Thr 695 | Trp | Ser | Ala | Val | Val 700 | Asn | Gly | Phe | Gly |
| Gly 705 | Met | Arg | Val | Tyr | Thr 710 | Asn | Glu | Leu | His | Phe 715 | Glu | Pro | Arg | Leu | Pro 720 |
| Lys | Glu | Trp | Asn | Leu 725 | Leu | Ser | Phe | Asn | Val 730 | Arg | Tyr | Lys | Gly | Arg 735 | Lys |
| Ile | Asn | Val | Lys 740 | Leu | Thr | Lys | Glu | Asn 745 | Val | Val | Phe | Ala | Leu 750 | Leu | Glu |
| Gly | Glu | Pro 755 | Ile | Glu | Ile | Tyr | Tyr 760 | Phe | Asp | Lys | Lys | Ile 765 | Leu | Leu | Glu |
| Lys | Gly | Glu | Ile | Lys 770 | | | | | | | | | | | |

( 2 ) INFORMATION FOR SEQ ID NO:5:

( i ) SEQUENCE CHARACTERISTICS:
    ( A ) LENGTH:2319 base pairs
    ( B ) TYPE:nucleic acid
    ( C ) STRANDEDNESS:double
    ( D ) TOPOLOGY:linear ( x i ) SEQUENCE DESCRIPTION:SEQ ID NO:5:

| | | | | | | |
|---|---|---|---|---|---|---|
| GCCAACAAAA | CGAAGAAACC | AATTTACCCT | TTTGAAGATT | GGGTTATAAG | AGAGACGCAG | 60 |
| TTTAGTATAG | ATACTAACTA | TAGAAATGAA | ACTATTTTTA | CTTTAGCAAA | TGGATATATT | 120 |
| GGAATGAGAG | GAACTTTTGA | GGAAAGATAT | TCAGGGCCTA | AAAATACTTC | TTTTAATGGG | 180 |
| ACGTATATCA | ATGGGTTTTA | TGAAATACAC | GATATAGTTT | ACCCTGAAGG | GGGATATGGT | 240 |
| TTTGCAAAAA | TAGGGCAGAC | GATGCTAAAT | GTTGCTGATA | GCAAAATAAT | AAAATTATAT | 300 |
| GTAGATGGGG | AAGAGTTTGA | TTTGTTACAA | GGGAAAATCC | TCTTTTATGA | GAGAGTACTT | 360 |

| | | | | | |
|---|---|---|---|---|---|
| GACATGAAGA | AAGGTTTTGT | AGAAAGAAAA | GTAAAATGGG | AATCCCCTAC | AGGAAAAATT | 420
| TTAGAGGTAA | AAATAAAGAG | AATTGTATCA | TTAAATAGAC | AACATTTAGC | GGCGATTTCT | 480
| TTTACTATGC | AACCTGTAAA | TTTTACCGGA | AAAATTAGAT | TTGTTTCCGC | TATTGACGGA | 540
| AATGTTTCAA | ATATAAATGA | TAGTGAAGAT | GTAAGAGTAG | GGTCAAATTT | AAAAGGAAAG | 600
| GTTTTAAAGA | CTATAGATAA | AAGTGTAGAG | GGTTTAAAAG | GGTGGATTGT | TCAAAAGACA | 660
| CAAAGAGCA | ATTTCTCCTA | TGCTTGCGCG | ATAGACAATG | TATTAGTGGC | AGATAGCAAA | 720
| TATGAAGTCT | CAAATAGTTT | AGAAGAAGAT | GGAGTAAAAG | TAATTGTAGA | TCTAGAGGCT | 780
| GAAAAAGGCA | CCTCATACAC | TTTGAATAAA | TTTATTTCCT | ATTACACTTC | AAAGGATTTT | 840
| GATGAAAATA | AATTGGTTGC | TCTTGCTTTA | GAAGAAATAG | AAAAAGCCAA | AAATGACGGC | 900
| TTTGAAACGA | TAGAAAAAGA | GCAGGAAGAA | TTTTTGAATT | CTTTTTGGAA | AGATGCTGAT | 960
| GTAATCATAG | AAGGAGATAA | AGCTCTGCAG | CAAGGCATAC | GCTTAATGA | ATTTCATCTA | 1020
| CTTCAATCTG | TCGGAAGAGA | TGGAAAGACA | AATATTGCAG | CAAAGGGCT | GACTGGAGGA | 1080
| GGTTATGAAG | GCCATTATTT | TTGGGATTCT | GATATCTATA | TAATGCCTTT | CTTTCTTTAT | 1140
| ACAAAGCCTG | AAATTGCAAA | AGCTTTGGTA | ATGTACAGGT | ATAATCTTTT | GGATGCAGCA | 1200
| AGATCCAGGG | CAAAGGAATT | AGGTCACAAA | GGAGCTTTGT | ATCCTTGGAG | AACGATAGAT | 1260
| GGTCCTGAAT | GTTCTGCTTA | CTTTCCAGCT | GGTACGGCAC | AGTATCACAT | AAATGCTGAT | 1320
| ATAGTTTATG | CTTTGAAAAG | ATATGTAGAA | GCGACGAATG | ACGTGGATTT | TCTTTATGAC | 1380
| TACGGTTGTG | AAATATTATT | TGAAACTGCA | AGATTTTGGG | AAGATTTAGG | AGCGTATATT | 1440
| CCTCTTAAGG | GCAATAAATT | CTGCATAAAC | TGTGTCACTG | GTCCGGATGA | GTATACGGCA | 1500
| TTAGTTGACA | ATAACGCTTA | TACCAATTAT | ATGGCGAAAA | TGAATTTGGA | ATATGCCTAT | 1560
| GACATTGCAA | ACAAAATGAA | AAAAGAAGTG | CCTCAAAAAT | ATCAAAAAGT | CGCTTCTAAA | 1620
| CTAAATCTAA | AGGATGAAGA | AATTGTTGCG | TGGAAAAAAG | CTGCTGACAA | TATGTACCTT | 1680
| CCTTATTCAA | AAGAACTTGA | TATTATACCA | CAGGATGACA | GTTTTTGTA | TAAAGAAAGG | 1740
| ATAACAGTGG | ATGAAATACC | TGAGGACCAA | TTTCCACTTT | TATTGCACTG | GCATTACCTA | 1800
| AATATTTACA | GATATCAAAT | ATGCAAACAG | CCTGATGTGT | TGCTTTTGAT | GTTTTTACAG | 1860
| AGAGAAAAAT | TTACTAAAGA | TGAACTTAAA | AAGAATTACG | ATTATTATGA | ACCTATTACC | 1920
| ACTCACGACT | CCTCCTTGTC | GCCAGCTATA | TTTAGCATAC | TAGCCAATGA | AATAGGATAT | 1980
| ACTGACAAGG | CTTATAAATA | CTTTATGATG | ACTGCAAGAA | TGGATTTGGA | TGACTACAAT | 2040
| GACAATGTTA | AGGACGGAAT | TCACGCTGCT | TCTATGGCAG | GGACATGGAG | CGCAGTTGTG | 2100
| AATGGTTTTG | GTGGAATGAG | GGTTTATACA | AATGAACTGC | ATTTTGAGCC | GAGATTGCCA | 2160
| AAAGAATGGA | ATTTGCTCTC | TTTTAATGTG | AGATACAAAG | GGAGAAAAAT | AAATGTCAAA | 2220
| TTAACCAAAG | AAAATGTTGT | GTTTGCATTA | TTAGAAGGAG | AGCCTATAGA | AATCTACTAC | 2280
| TTTGACAAAA | AAATTTTACT | TGAAAAAGGA | GAAATAAAG | | | 2319

( 2 ) INFORMATION FOR SEQ ID NO:6:

( i ) SEQUENCE CHARACTERISTICS:
        ( A ) LENGTH:30 amino acids
        ( B ) TYPE:amino acid
        ( D ) TOPOLOGY:linear ( i i ) MOLECULE TYPE:peptide ( v ) FRAGMENT TYPE:N-terminal fragment ( x i ) SEQUENCE DESCRIPTION:SEQ ID NO:6:

|   |   |   |   |   |   |   |   |   |   |   |   |   |   |   |
|---|---|---|---|---|---|---|---|---|---|---|---|---|---|---|
| Ala | Asn | Lys | Thr | Lys | Lys | Pro | Ile | Tyr | Pro | Phe | Glu | Asp | Trp | Val | Ile |
| 1 |   |   |   | 5 |   |   |   |   | 10 |   |   |   |   | 15 |
| Arg | Glu | Thr | Gln | Phe | Ser | Ile | Asp | Thr | Asn | Tyr | Arg | Asn | Glu |
|   |   |   | 20 |   |   |   |   | 25 |   |   |   |   | 30 |

(2) INFORMATION FOR SEQ ID NO:7:

(i) SEQUENCE CHARACTERISTICS:
        (A) LENGTH:15 amino acids
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:7:

|   |   |   |   |   |   |   |   |   |   |   |   |   |   |   |
|---|---|---|---|---|---|---|---|---|---|---|---|---|---|---|
| Asn | Tyr | Asp | Tyr | Tyr | Glu | Pro | Ile | Thr | Thr | His | Asp | Ser | Ser | Leu |
| 1 |   |   |   | 5 |   |   |   |   | 10 |   |   |   |   | 15 |

(2) INFORMATION FOR SEQ ID NO:8:

(i) SEQUENCE CHARACTERISTICS:
        (A) LENGTH:3345 base pairs
        (B) TYPE:nucleic acid
        (C) STRANDEDNESS:double
        (D) TOPOLOGY:linear (ii) MOLECULE TYPE:Genomic DNA (vi) ORIGINAL SOURCE:
        (A) ORGANISM:Thermoanaerobium brockii
        (F) STRAIN:ATCC 35047

(ix) FEATURE:
        (A1) NAME/KEY:1-595 5'- UTR
        (C1) IDENTIFICATION METHOD:E
        (A2) NAME/KEY:596-2917 mat peptide
        (C2) IDENTIFICATION METHOD:S
        (A3) NAME/KEY:2918-3345 3'- UTR
        (C3) IDENTIFICATION METHOD:E (xi) SEQUENCE DESCRIPTION:SEQ ID NO:8:

```
CTGACTGGAA  TACACCTGTA  GAATATCTTG  CAAAAGAGAG  CGTATATTTG  GTTCAAAATT     60

GGCCGTACAC  TGCAAACGTT  CTTGTAGAGC  AGTATGGAAA  AAAGAACATT  TTGGCATATC    120

ACGGATGGAC  AGGTCCGGTT  AAAGAGTCCC  ACGTTTTGGG  AGGAGAAGTT  ATAGGAATAC    180

CAACTGGTGC  ACCTAATAAA  GAGATGGCTA  TAAAGTTTAT  GGAATACCTT  ATGAGTAAAG    240

AAGTTCAAGA  GAAACTTGTC  ACTAAATTAG  GATGGCCATC  CATGAGAAGT  GACGCTTATG    300

GGAAGGTTGC  AGAGTGGCAA  AAACCATATT  TTGAAGCTAT  AAATGAAGCG  TTAAAACATG    360

CAGAACCAAG  GCCAAACCTT  GTATACTGGG  CTGATGTGGA  CAAAGCTATA  AATGGAGCAT    420

TGAGAGAAAT  AATATTTGAA  GGCAAAGATA  TCAAGACAAC  TCTTGACAAA  TATCACAACA    480

TGATAGAAGA  AGCTAAGAAA  GCTGCAGAAA  GCAAGTAAAT  GTTTTAAATT  GTTTTAGTCG    540

GAAACGACTT  TGTTTCCGAC  TAAAATTTTG  AATAAAGTAA  GAGTGGAGGA  TGGAT         595
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| ATG | GCC | AAC | AAA | ACG | AAG | AAA | CCA | ATT | TAC | CCT | TTT | GAA | GAT | TGG | GTT | 643 |
| Met | Ala | Asn | Lys | Thr | Lys | Lys | Pro | Ile | Tyr | Pro | Phe | Glu | Asp | Trp | Val |     |
| 1   |     |     |     | 5   |     |     |     |     | 10  |     |     |     |     | 15  |     |     |
| ATA | AGA | GAG | ACG | CAG | TTT | AGT | ATA | GAT | ACT | AAC | TAT | AGA | AAT | GAA | ACT | 691 |
| Ile | Arg | Glu | Thr | Gln | Phe | Ser | Ile | Asp | Thr | Asn | Tyr | Arg | Asn | Glu | Thr |     |
|     |     |     | 20  |     |     |     |     | 25  |     |     |     |     | 30  |     |     |     |
| ATT | TTT | ACT | TTA | GCA | AAT | GGA | TAT | ATT | GGA | ATG | AGA | GGA | ACT | TTT | GAG | 739 |
| Ile | Phe | Thr | Leu | Ala | Asn | Gly | Tyr | Ile | Gly | Met | Arg | Gly | Thr | Phe | Glu |     |
|     |     |     | 35  |     |     |     |     | 40  |     |     |     |     | 45  |     |     |     |

```
GAA AGA TAT TCA GGG CCT AAA AAT ACT TCT TTT AAT GGG ACG TAT ATC      787
Glu Arg Tyr Ser Gly Pro Lys Asn Thr Ser Phe Asn Gly Thr Tyr Ile
    50              55                  60

AAT GGG TTT TAT GAA ATA CAC GAT ATA GTT TAC CCT GAA GGG GGA TAT      835
Asn Gly Phe Tyr Glu Ile His Asp Ile Val Tyr Pro Glu Gly Gly Tyr
65              70                  75                  80

GGT TTT GCA AAA ATA GGG CAG ACG ATG CTA AAT GTT GCT GAT AGC AAA      883
Gly Phe Ala Lys Ile Gly Gln Thr Met Leu Asn Val Ala Asp Ser Lys
                85                  90                  95

ATA ATA AAA TTA TAT GTA GAT GGG GAA GAG TTT GAT TTG TTA CAA GGG      931
Ile Ile Lys Leu Tyr Val Asp Gly Glu Glu Phe Asp Leu Leu Gln Gly
            100                 105                 110

AAA ATC CTC TTT TAT GAG AGA GTA CTT GAC ATG AAG AAA GGT TTT GTA      979
Lys Ile Leu Phe Tyr Glu Arg Val Leu Asp Met Lys Lys Gly Phe Val
        115                 120                 125

GAA AGA AAA GTA AAA TGG GAA TCC CCT ACA GGA AAA ATT TTA GAG GTA     1027
Glu Arg Lys Val Lys Trp Glu Ser Pro Thr Gly Lys Ile Leu Glu Val
    130                 135                 140

AAA ATA AAG AGA ATT GTA TCA TTA AAT AGA CAA CAT TTA GCG GCG ATT     1075
Lys Ile Lys Arg Ile Val Ser Leu Asn Arg Gln His Leu Ala Ala Ile
145                 150                 155                 160

TCT TTT ACT ATG CAA CCT GTA AAT TTT ACC GGA AAA ATT AGA TTT GTT     1123
Ser Phe Thr Met Gln Pro Val Asn Phe Thr Gly Lys Ile Arg Phe Val
                165                 170                 175

TCC GCT ATT GAC GGA AAT GTT TCA AAT ATA AAT GAT AGT GAA GAT GTA     1171
Ser Ala Ile Asp Gly Asn Val Ser Asn Ile Asn Asp Ser Glu Asp Val
            180                 185                 190

AGA GTA GGG TCA AAT TTA AAA GGA AAG GTT TTA AAG ACT ATA GAT AAA     1219
Arg Val Gly Ser Asn Leu Lys Gly Lys Val Leu Lys Thr Ile Asp Lys
        195                 200                 205

AGT GTA GAG GGT TTA AAA GGG TGG ATT GTT CAA AAG ACA CAA AAG AGC     1267
Ser Val Glu Gly Leu Lys Gly Trp Ile Val Gln Lys Thr Gln Lys Ser
    210                 215                 220

AAT TTC TCC TAT GCT TGC GCG ATA GAC AAT GTA TTA GTG GCA GAT AGC     1315
Asn Phe Ser Tyr Ala Cys Ala Ile Asp Asn Val Leu Val Ala Asp Ser
225                 230                 235                 240

AAA TAT GAA GTC TCA AAT AGT TTA GAA GAA GAT GGA GTA AAA GTA ATT     1363
Lys Tyr Glu Val Ser Asn Ser Leu Glu Glu Asp Gly Val Lys Val Ile
                245                 250                 255

GTA GAT CTA GAG GCT GAA AAA GGC ACC TCA TAC ACT TTG AAT AAA TTT     1411
Val Asp Leu Glu Ala Glu Lys Gly Thr Ser Tyr Thr Leu Asn Lys Phe
            260                 265                 270

ATT TCC TAT TAC ACT TCA AAG GAT TTT GAT GAA AAT AAA TTG GTT GCT     1459
Ile Ser Tyr Tyr Thr Ser Lys Asp Phe Asp Glu Asn Lys Leu Val Ala
        275                 280                 285

CTT GCT TTA GAA GAA ATA GAA AAA GCC AAA AAT GAC GGC TTT GAA ACG     1507
Leu Ala Leu Glu Glu Ile Glu Lys Ala Lys Asn Asp Gly Phe Glu Thr
    290                 295                 300

ATA GAA AAA GAG CAG GAA GAA TTT TTG AAT TCT TTT TGG AAA GAT GCT     1555
Ile Glu Lys Glu Gln Glu Glu Phe Leu Asn Ser Phe Trp Lys Asp Ala
305                 310                 315                 320

GAT GTA ATC ATA GAA GGA GAT AAA GCT CTG CAG CAA GGC ATA CGC TTT     1603
Asp Val Ile Ile Glu Gly Asp Lys Ala Leu Gln Gln Gly Ile Arg Phe
                325                 330                 335

AAT GAA TTT CAT CTA CTT CAA TCT GTC GGA AGA GAT GGA AAG ACA AAT     1651
Asn Glu Phe His Leu Leu Gln Ser Val Gly Arg Asp Gly Lys Thr Asn
            340                 345                 350

ATT GCA GCA AAA GGG CTG ACT GGA GGA GGT TAT GAA GGC CAT TAT TTT     1699
Ile Ala Ala Lys Gly Leu Thr Gly Gly Gly Tyr Glu Gly His Tyr Phe
        355                 360                 365
```

| | | | | | | | | | | | | | | | | |
|---|---|---|---|---|---|---|---|---|---|---|---|---|---|---|---|---|
| TGG | GAT | TCT | GAT | ATC | TAT | ATA | ATG | CCT | TTC | TTT | CTT | TAT | ACA | AAG | CCT | 1747 |
| Trp | Asp | Ser | Asp | Ile | Tyr | Ile | Met | Pro | Phe | Phe | Leu | Tyr | Thr | Lys | Pro | |
| | 370 | | | | 375 | | | | | 380 | | | | | | |
| GAA | ATT | GCA | AAA | GCT | TTG | GTA | ATG | TAC | AGG | TAT | AAT | CTT | TTG | GAT | GCA | 1795 |
| Glu | Ile | Ala | Lys | Ala | Leu | Val | Met | Tyr | Arg | Tyr | Asn | Leu | Leu | Asp | Ala | |
| 385 | | | | | 390 | | | | | 395 | | | | | 400 | |
| GCA | AGA | TCC | AGG | GCA | AAG | GAA | TTA | GGT | CAC | AAA | GGA | GCT | TTG | TAT | CCT | 1843 |
| Ala | Arg | Ser | Arg | Ala | Lys | Glu | Leu | Gly | His | Lys | Gly | Ala | Leu | Tyr | Pro | |
| | | | | 405 | | | | | 410 | | | | | 415 | | |
| TGG | AGA | ACG | ATA | GAT | GGT | CCT | GAA | TGT | TCT | GCT | TAC | TTT | CCA | GCT | GGT | 1891 |
| Trp | Arg | Thr | Ile | Asp | Gly | Pro | Glu | Cys | Ser | Ala | Tyr | Phe | Pro | Ala | Gly | |
| | | | 420 | | | | | 425 | | | | | 430 | | | |
| ACG | GCA | CAG | TAT | CAC | ATA | AAT | GCT | GAT | ATA | GTT | TAT | GCT | TTG | AAA | AGA | 1939 |
| Thr | Ala | Gln | Tyr | His | Ile | Asn | Ala | Asp | Ile | Val | Tyr | Ala | Leu | Lys | Arg | |
| | | 435 | | | | | 440 | | | | | 445 | | | | |
| TAT | GTA | GAA | GCG | ACG | AAT | GAC | GTG | GAT | TTT | CTT | TAT | GAC | TAC | GGT | TGT | 1987 |
| Tyr | Val | Glu | Ala | Thr | Asn | Asp | Val | Asp | Phe | Leu | Tyr | Asp | Tyr | Gly | Cys | |
| | 450 | | | | | 455 | | | | | 460 | | | | | |
| GAA | ATA | TTA | TTT | GAA | ACT | GCA | AGA | TTT | TGG | GAA | GAT | TTA | GGA | GCG | TAT | 2035 |
| Glu | Ile | Leu | Phe | Glu | Thr | Ala | Arg | Phe | Trp | Glu | Asp | Leu | Gly | Ala | Tyr | |
| 465 | | | | | 470 | | | | | 475 | | | | | 480 | |
| ATT | CCT | CTT | AAG | GGC | AAT | AAA | TTC | TGC | ATA | AAC | TGT | GTC | ACT | GGT | CCG | 2083 |
| Ile | Pro | Leu | Lys | Gly | Asn | Lys | Phe | Cys | Ile | Asn | Cys | Val | Thr | Gly | Pro | |
| | | | | 485 | | | | | 490 | | | | | 495 | | |
| GAT | GAG | TAT | ACG | GCA | TTA | GTT | GAC | AAT | AAC | GCT | TAT | ACC | AAT | TAT | ATG | 2131 |
| Asp | Glu | Tyr | Thr | Ala | Leu | Val | Asp | Asn | Asn | Ala | Tyr | Thr | Asn | Tyr | Met | |
| | | | 500 | | | | | 505 | | | | | 510 | | | |
| GCG | AAA | ATG | AAT | TTG | GAA | TAT | GCC | TAT | GAC | ATT | GCA | AAC | AAA | ATG | AAA | 2179 |
| Ala | Lys | Met | Asn | Leu | Glu | Tyr | Ala | Tyr | Asp | Ile | Ala | Asn | Lys | Met | Lys | |
| | | 515 | | | | | 520 | | | | | 525 | | | | |
| AAA | GAA | GTG | CCT | CAA | AAA | TAT | CAA | AAA | GTC | GCT | TCT | AAA | CTA | AAT | CTA | 2227 |
| Lys | Glu | Val | Pro | Gln | Lys | Tyr | Gln | Lys | Val | Ala | Ser | Lys | Leu | Asn | Leu | |
| | 530 | | | | | 535 | | | | | 540 | | | | | |
| AAG | GAT | GAA | GAA | ATT | GTT | GCG | TGG | AAA | AAA | GCT | GCT | GAC | AAT | ATG | TAC | 2275 |
| Lys | Asp | Glu | Glu | Ile | Val | Ala | Trp | Lys | Lys | Ala | Ala | Asp | Asn | Met | Tyr | |
| 545 | | | | | 550 | | | | | 555 | | | | | 560 | |
| CTT | CCT | TAT | TCA | AAA | GAA | CTT | GAT | ATT | ATA | CCA | CAG | GAT | GAC | AGT | TTT | 2323 |
| Leu | Pro | Tyr | Ser | Lys | Glu | Leu | Asp | Ile | Ile | Pro | Gln | Asp | Asp | Ser | Phe | |
| | | | | 565 | | | | | 570 | | | | | 575 | | |
| TTG | TAT | AAA | GAA | AGG | ATA | ACA | GTG | GAT | GAA | ATA | CCT | GAG | GAC | CAA | TTT | 2371 |
| Leu | Tyr | Lys | Glu | Arg | Ile | Thr | Val | Asp | Glu | Ile | Pro | Glu | Asp | Gln | Phe | |
| | | | 580 | | | | | 585 | | | | | 590 | | | |
| CCA | CTT | TTA | TTG | CAC | TGG | CAT | TAC | CTA | AAT | ATT | TAC | AGA | TAT | CAA | ATA | 2419 |
| Pro | Leu | Leu | Leu | His | Trp | His | Tyr | Leu | Asn | Ile | Tyr | Arg | Tyr | Gln | Ile | |
| | | 595 | | | | | 600 | | | | | 605 | | | | |
| TGC | AAA | CAG | CCT | GAT | GTG | TTG | CTT | TTG | ATG | TTT | TTA | CAG | AGA | GAA | AAA | 2467 |
| Cys | Lys | Gln | Pro | Asp | Val | Leu | Leu | Leu | Met | Phe | Leu | Gln | Arg | Glu | Lys | |
| | 610 | | | | | 615 | | | | | 620 | | | | | |
| TTT | ACT | AAA | GAT | GAA | CTT | AAA | AAG | AAT | TAC | GAT | TAT | TAT | GAA | CCT | ATT | 2515 |
| Phe | Thr | Lys | Asp | Glu | Leu | Lys | Lys | Asn | Tyr | Asp | Tyr | Tyr | Glu | Pro | Ile | |
| 625 | | | | | 630 | | | | | 635 | | | | | 640 | |
| ACC | ACT | CAC | GAC | TCC | TCC | TTG | TCG | CCA | GCT | ATA | TTT | AGC | ATA | CTA | GCC | 2563 |
| Thr | Thr | His | Asp | Ser | Ser | Leu | Ser | Pro | Ala | Ile | Phe | Ser | Ile | Leu | Ala | |
| | | | | 645 | | | | | 650 | | | | | 655 | | |
| AAT | GAA | ATA | GGA | TAT | ACT | GAC | AAG | GCT | TAT | AAA | TAC | TTT | ATG | ATG | ACT | 2611 |
| Asn | Glu | Ile | Gly | Tyr | Thr | Asp | Lys | Ala | Tyr | Lys | Tyr | Phe | Met | Met | Thr | |
| | | | 660 | | | | | 665 | | | | | 670 | | | |
| GCA | AGA | ATG | GAT | TTG | GAT | GAC | TAC | AAT | GAC | AAT | GTT | AAG | GAC | GGA | ATT | 2659 |
| Ala | Arg | Met | Asp | Leu | Asp | Asp | Tyr | Asn | Asp | Asn | Val | Lys | Asp | Gly | Ile | |
| | | 675 | | | | | 680 | | | | | 685 | | | | |

-continued

| | | | | | | | | | | | | | | | |
|---|---|---|---|---|---|---|---|---|---|---|---|---|---|---|---|
| CAC | GCT | GCT | TCT | ATG | GCA | GGG | ACA | TGG | AGC | GCA | GTT | GTG | AAT | GGT | TTT | 2707
| His | Ala | Ala | Ser | Met | Ala | Gly | Thr | Trp | Ser | Ala | Val | Val | Asn | Gly | Phe |
| | 690 | | | | | 695 | | | | | 700 | | | | |
| GGT | GGA | ATG | AGG | GTT | TAT | ACA | AAT | GAA | CTG | CAT | TTT | GAG | CCG | AGA | TTG | 2755
| Gly | Gly | Met | Arg | Val | Tyr | Thr | Asn | Glu | Leu | His | Phe | Glu | Pro | Arg | Leu |
| 705 | | | | | 710 | | | | | 715 | | | | | 720 |
| CCA | AAA | GAA | TGG | AAT | TTG | CTC | TCT | TTT | AAT | GTG | AGA | TAC | AAA | GGG | AGA | 2803
| Pro | Lys | Glu | Trp | Asn | Leu | Leu | Ser | Phe | Asn | Val | Arg | Tyr | Lys | Gly | Arg |
| | | | | 725 | | | | | 730 | | | | | 735 | |
| AAA | ATA | AAT | GTC | AAA | TTA | ACC | AAA | GAA | AAT | GTT | GTG | TTT | GCA | TTA | TTA | 2851
| Lys | Ile | Asn | Val | Lys | Leu | Thr | Lys | Glu | Asn | Val | Val | Phe | Ala | Leu | Leu |
| | | | 740 | | | | | 745 | | | | | 750 | | |
| GAA | GGA | GAG | CCT | ATA | GAA | ATC | TAC | TAC | TTT | GAC | AAA | AAA | ATT | TTA | CTT | 2899
| Glu | Gly | Glu | Pro | Ile | Glu | Ile | Tyr | Tyr | Phe | Asp | Lys | Lys | Ile | Leu | Leu |
| | | 755 | | | | | 760 | | | | | 765 | | | |
| GAA | AAA | GGA | GAA | ATA | AAG | | | | | | | | | | | 2917
| Glu | Lys | Gly | Glu | Ile | Lys | | | | | | | | | | |
| | 770 | | | | | | | | | | | | | | |

| | | | | | |
|---|---|---|---|---|---|
| TAGAAAGTCT | CAAAAATTAA | AGAAGTATGG | AGCCATTGGC | ACCATACTTC | TTTAATTTTT | 2977
| TTATATGTCG | TTACTTGAAA | GGGTGAGTGA | CCCGCCTCCT | ACACTTAAAT | CAAAGTAATA | 3037
| ATCTCCACTG | CCTCGGAAGG | AATATACTTT | GATATAATAG | GTTCCCGTTT | GTGTTGGAAT | 3097
| GTATGTTATT | GTCTCCTGCC | TTTGTGTTCC | AGTTGAACTT | TGACAAGAG | TACCAGTTGG | 3157
| GTCATAGAGG | TATATATCGA | AATCAGGGTT | ATAGTTTGCC | CAATCAGGTA | TTATGAAAGT | 3217
| TATTGCAATA | GGATATGATG | TGTCTGTCAC | ATTAAATGTC | CAAATGTCAC | TGTAACGAGA | 3277
| CCCAGGAAGT | GACTCTTTAG | CATAATAGTG | GTTTGGCGCA | GATATATTAG | TTCCTGTGAA | 3337
| ATTTCCAG | | | | | | 3345

( 2 ) INFORMATION FOR SEQ ID NO:9:

( i ) SEQUENCE CHARACTERISTICS:
        ( A ) LENGTH:20 base pairs
        ( B ) TYPE:nucleic acid
        ( C ) STRANDEDNESS:double
        ( D ) TOPOLOGY:linear ( x i ) SEQUENCE DESCRIPTION:SEQ ID NO:9:

TAYCCNTTYG ARGAYTGGGT                                          20

( 2 ) INFORMATION FOR SEQ ID NO:10:

( i ) SEQUENCE CHARACTERISTICS:
        ( A ) LENGTH:20 base pairs
        ( B ) TYPE:nucleic acid
        ( C ) STRANDEDNESS:double
        ( D ) TOPOLOGY:linear ( x i ) SEQUENCE DESCRIPTION:SEQ ID NO:10:

AAYTAYGAYT AYTAYGARCC                                          20